US009216063B2

(12) United States Patent
Frey et al.

(10) Patent No.: US 9,216,063 B2
(45) Date of Patent: Dec. 22, 2015

(54) APPARATUS AND METHOD FOR COLLECTING REUSABLE MATERIAL AND CLEANING SURGICAL INSTRUMENTS

(71) Applicants: George Frey, Englewood, CO (US); Benjamin Majors, Denver, CO (US); Charles O'Neil, Littleton, CO (US); Geoff Lai, Lakewood, CO (US); Russ Rydin, Highlands Ranch, CO (US)

(72) Inventors: George Frey, Englewood, CO (US); Benjamin Majors, Denver, CO (US); Charles O'Neil, Littleton, CO (US); Geoff Lai, Lakewood, CO (US); Russ Rydin, Highlands Ranch, CO (US)

( * ) Notice: Subject to any disclaimer, the term of this patent is extended or adjusted under 35 U.S.C. 154(b) by 154 days.

(21) Appl. No.: 14/133,146

(22) Filed: Dec. 18, 2013

(65) Prior Publication Data
US 2014/0165309 A1 Jun. 19, 2014

Related U.S. Application Data

(60) Provisional application No. 61/738,939, filed on Dec. 18, 2012.

(51) Int. Cl.
*A61B 19/00* (2006.01)
*A61B 10/02* (2006.01)
*A61B 17/00* (2006.01)

(52) U.S. Cl.
CPC ............... *A61B 19/34* (2013.01); *A61B 10/025* (2013.01); *A61B 2017/00969* (2013.01)

(58) Field of Classification Search
CPC ........... A61B 19/34; A61B 2200/3073; A47L 21/02; A47L 21/00; B08B 1/002; A46B 11/06; A46B 11/00

USPC ......... 15/21.1, 88, 88.2–88.3, 104.04, 104.8, 15/104.92, 159.1, 160; 600/578
See application file for complete search history.

(56) References Cited

U.S. PATENT DOCUMENTS

| 2,478,522 | A | * | 8/1949 | Buskirk .......................... 15/106 |
| 3,044,089 | A | * | 7/1962 | Boynton ........................ 15/21.2 |
| 5,093,079 | A | | 3/1992 | Bakaitis et al. |
| 5,308,406 | A | * | 5/1994 | Wallock et al. ................. 134/42 |
| 5,384,933 | A | * | 1/1995 | Wang .............................. 15/311 |
| 5,471,706 | A | | 12/1995 | Wallock et al. |
| 6,745,424 | B1 | | 6/2004 | Pimentel et al. |
| 6,908,247 | B2 | | 6/2005 | Gomez |
| 7,518,598 | B2 | | 4/2009 | Liu |
| 7,658,610 | B2 | | 2/2010 | Knopp |
| 7,844,356 | B2 | | 11/2010 | Matov et al. |

(Continued)

FOREIGN PATENT DOCUMENTS

| EP | 1125587 | 8/2001 |
| WO | WO 2007/137234 | 11/2007 |

(Continued)

OTHER PUBLICATIONS

International Search Report and Written Opinion for International (PCT) Patent Application No. PCT/US13/6129, mailed Mar. 31, 2014 7 pages.

*Primary Examiner* — Laura C Guidotti
(74) *Attorney, Agent, or Firm* — Sheridan Ross P.C.

(57) ABSTRACT

A system and method for cleaning instruments, which provides removal and collection of material from one or more surgical instruments. The cleaning apparatus may be a dry cleaning process or offered in conjunction with one or more fluids. In one embodiment, the cleaning apparatus continuously purges blood, bone and other debris quickly and may comprise a system for removing reusable material from the cleaning process for reuse.

21 Claims, 14 Drawing Sheets

(56) References Cited

U.S. PATENT DOCUMENTS

| | | |
|---|---|---|
| 7,957,824 B2 | 6/2011 | Boronvinskih et al. |
| 7,982,885 B2 | 7/2011 | Lapstun et al. |
| 2008/0114370 A1 | 5/2008 | Schoenefeld |
| 2009/0087276 A1 | 4/2009 | Rose |
| 2009/0138020 A1 | 5/2009 | Park et al. |
| 2010/0217336 A1 | 8/2010 | Crawford et al. |
| 2010/0306936 A1* | 12/2010 | Hernandez et al. ........ 15/104.92 |
| 2012/0125378 A1 | 5/2012 | Burkholder et al. |
| 2013/0055514 A1 | 3/2013 | Grötsch |

FOREIGN PATENT DOCUMENTS

| | | |
|---|---|---|
| WO | WO 2009/091709 | 7/2009 |
| WO | WO 2013/076026 | 5/2013 |

* cited by examiner

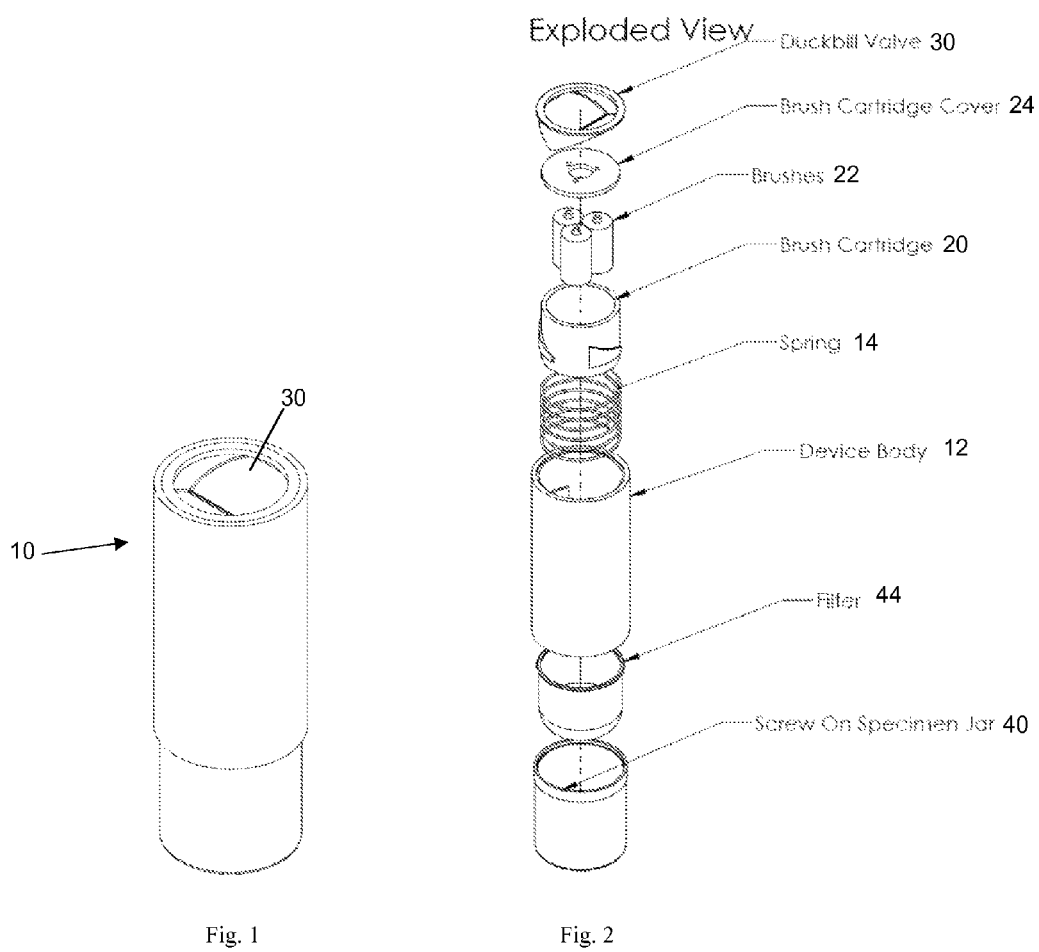

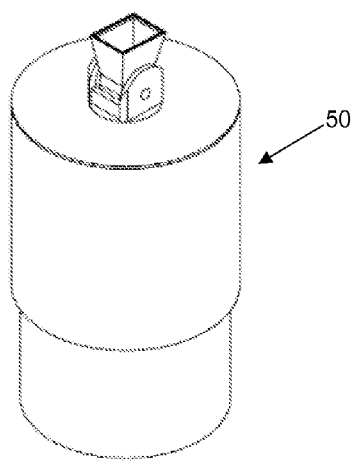
Fig. 5
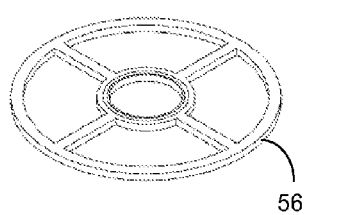
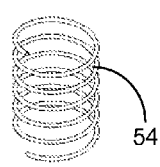
54
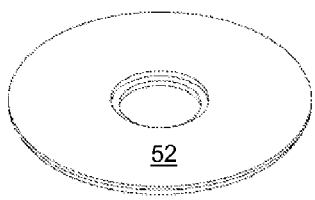
52
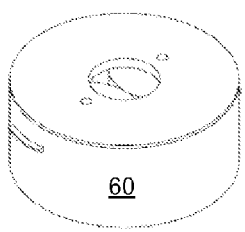
60
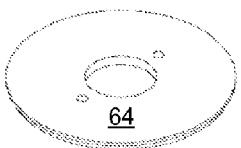
Brush Cartridge Cover
64
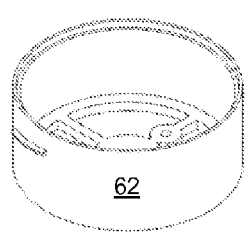
62
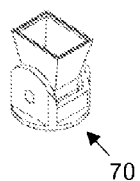
70
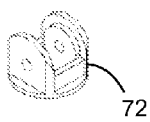
72
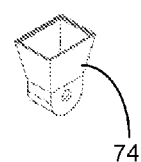
74
76
Fig. 6

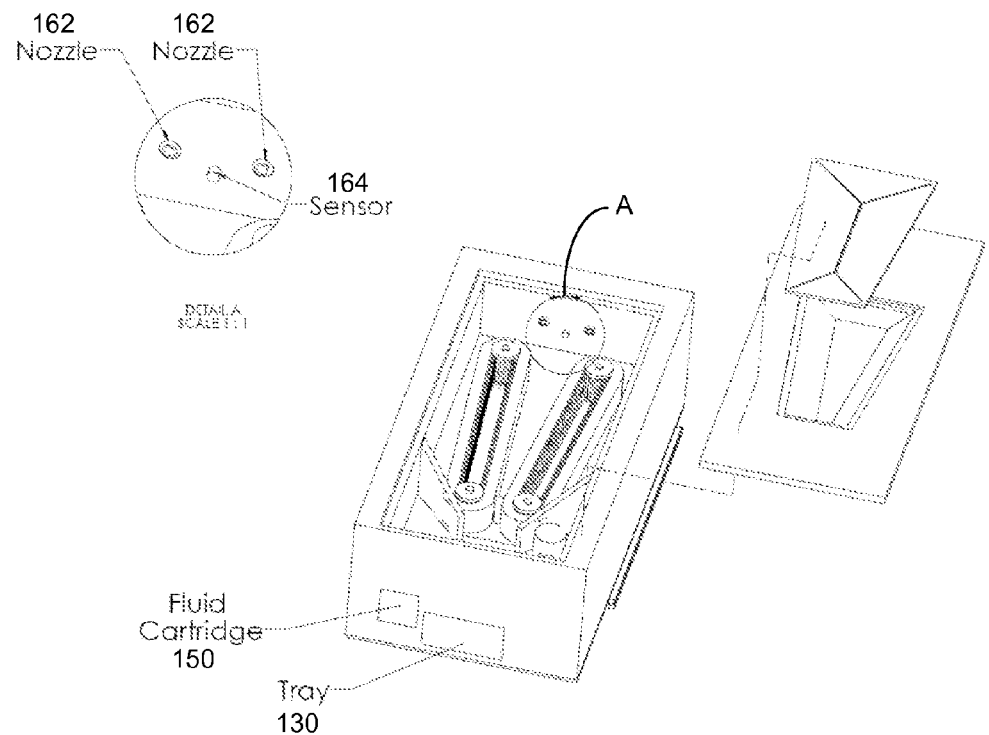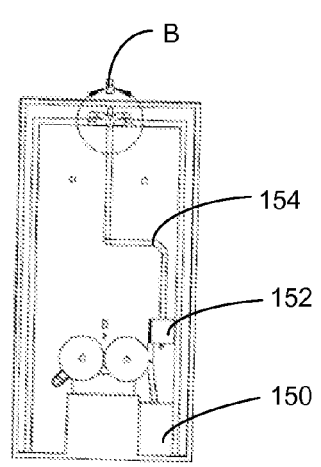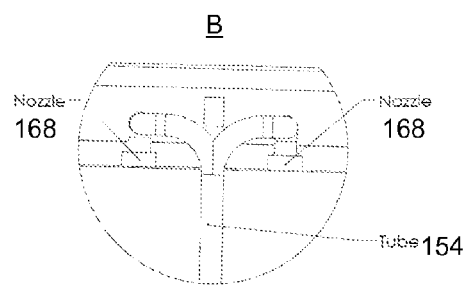
Fig. 12
Fig. 13
Fig. 14

APPARATUS AND METHOD FOR COLLECTING REUSABLE MATERIAL AND CLEANING SURGICAL INSTRUMENTS

CROSS-REFERENCE TO RELATED APPLICATIONS

The present application claims priority from U.S. Provisional Application No. 61/738,939, filed Dec. 18, 2012, the entire disclosure of which is hereby incorporated by reference.

FIELD OF THE INVENTION

The present disclosure relates to the field of medical devices and is generally directed toward apparatus for use with surgical instruments to clean and maintain sterility of surgical instruments, as well as apparatus for segregating usable materials from surgical instruments such as cortical and cancellous bone, and methods of using the same.

BACKGROUND OF THE INVENTION

There is presently a recognized shortcoming in the art of cleaning and sterilization of surgical tools, instruments and implants. More specifically, there is no apparatus presently available which permits a surgeon to clean a tool, instrument or implant, while at the same time segregating materials that the tool, instrument or implant is in contact with for reuse during the same or a different procedure. For example, when a surgical instrument is used for resection of a patient's boney anatomy, it is desirable for the surgeon to clean the instrument periodically, and is also desirable for the surgeon to collect the small pieces of the patient's boney anatomy for reuse, such as in a bone fusion or fracture repair.

Given the complexities of surgical procedures and the various tools, instruments, implants and other devices used in the procedures, as well as the varying anatomical differentiation among patients, it is often challenging to provide a surgeon with the necessary tools that may be used and maintained as sterile throughout a particular procedure without crowding the operating room with trays of unused instruments. It is also difficult to provide a method and system for safely and efficiently cleaning the variety of different sized and shaped instruments during the procedure. It is therefore desirable to provide an apparatus capable of cleaning a wide variety of instruments in an operating room that is predictable and repeatable and does not obstruct the surgeon or other professionals present during the surgery, and that may otherwise be secured to one or more surfaces in the operating room, all the while maintaining sterility.

It would therefore be advantageous to provide apparatus suitable for use with a variety of instruments used in surgical procedures that is adapted and/or configured and/or capable of cleaning and/or sterilizing the instrument and segregating, cleaning and preparing material that the instrument has come into contact with during the surgical procedure for reuse. It would also be advantageous to provide an apparatus that reduces, if not eliminates, the problems and risks noted above. Other advantages over the prior art will become known upon review of the Summary and Detailed Description of the Invention and the appended claims.

SUMMARY OF THE INVENTION

According to one aspect of the present disclosure, a novel apparatus and method is described for cleaning and/or sterilizing an instrument, which according to one preferred embodiment also comprises means for segregating, cleaning and preparing usable material in contact with an instrument for later use by the surgeon or other medical professional. The apparatus in one embodiment provides solutions to a number of problems experienced in the prior art, and in particular provides an apparatus that removes and collects certain material from one or more surgical instruments for reuse. The cleaning apparatus according to varying embodiments disclosed herein may dry or offered in conjunction with a pressurized liquid supply, or with a saline bath.

In one embodiment, the apparatus provides automated cleaning of the instruments by manual operation to purge blood, bone and other debris quickly and efficiently.

According to one embodiment, the cleaning apparatus comprises an unobtrusive power supply, which when in use does not distract the field of vision of the surgeon from the surgery. In one embodiment, the apparatus is electro-mechanically driven. In another embodiment, the apparatus is pneumatically driven.

According to one embodiment, the cleaning apparatus comprises a receiving face that has a tapered or funneled or "duck bill" shaped entry point, which can be oriented to any position, and permits a surgeon to guide the instrument into the cleaning apparatus without diverting his or her eyes from the surgical site. In certain embodiments, the receiving face is adjustable to permit orientation, extension and/or retraction, and in a plurality of directions relative to the body of the cleaning apparatus.

According to one particular embodiment, the instrument entry portal is oriented to grab and stabilize the instruments, which are often long and unbalanced, and permits the surgeon to leave the instrument at least partially within the cleaning apparatus for continued cleaning to enable the surgeon to free his hands temporarily while he uses another instrument. In one embodiment, an auditory or other signal may be provided to the surgeon once all debris has been sensed by the cleaning apparatus as having been removed from the instrument.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356 and 7,658,610, and U.S. Pat. Pub. Nos. 20100217336, 20090138020, 20090087276 and 20080114370.

One having skill in the art will appreciate that embodiments of the present disclosure may have various sizes. The sizes of the various elements of embodiments of the present disclosure may be sized based on various factors including, for example, the type or style of the instruments to be used in the surgical procedure, the anatomy of the patient or desired scope of the surgical procedure, the preferences of the surgeon or person using the apparatus, the surgical site location, physical features of the instruments used with the apparatus described herein, including, for example, width, length, shape, range of motion and thickness, and the size of the instruments to be used with the apparatus.

Embodiments of the present disclosure describe a multitude of attachments to stabilize the apparatus within the surgical field. This may include, by way of example but not limitation, direct attachment to an appropriately selected structure by magnetic attraction or by mechanical coupling to a surgical drape, frame or the operating table.

Embodiments of the present disclosure offer several advantages over the prior art including, for example, enhancing the speed and efficacy of the procedure, the ability to scavenge and separate tissue from the instrument, the disposability of certain instruments and/or implants, lower risk of infection, greater efficiency in completing a surgical procedure, more assistance for the surgeon from the physician's assistant, a more consistent and controlled method of cleaning an instrument via an apparatus (as opposed to an individual), and fewer and/or less expensive or complex instruments in a surgical site, among other advantages. Furthermore, by reducing the need for the constant passing of instruments between surgical personnel for cleaning may reduce the potential for injury.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, resins, particularly fiber-encased resinous materials rubber, latex, synthetic rubber, synthetic materials, polymers, and natural materials.

One having skill in the art will appreciate that embodiments of the present disclosure may be used in conjunction with devices that employ automated or semi-automated manipulation. Embodiments of the present disclosure may be designed such that the apparatus may be surgeon-driven, such as by a hand trigger or foot pedal, or may be automated by receiving an input from a photoelectric or proximity sensor detecting the presence of an instrument adjacent the apparatus, or alternatively controlled programmatically by a computer controller, by servo-controlled mechanisms, by hydraulically-driven mechanisms, by pneumatically-driven mechanisms or by piezoelectric actuators. It is expressly understood for purposes of this disclosure that other types of machinery may be employed in the systems and methods described herein.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

In the drawings:

FIG. 1 is a perspective view of a cleaning apparatus according to one embodiment of the present disclosure;

FIG. 2 is an exploded view of the apparatus shown in FIG. 1;

Figure 3:
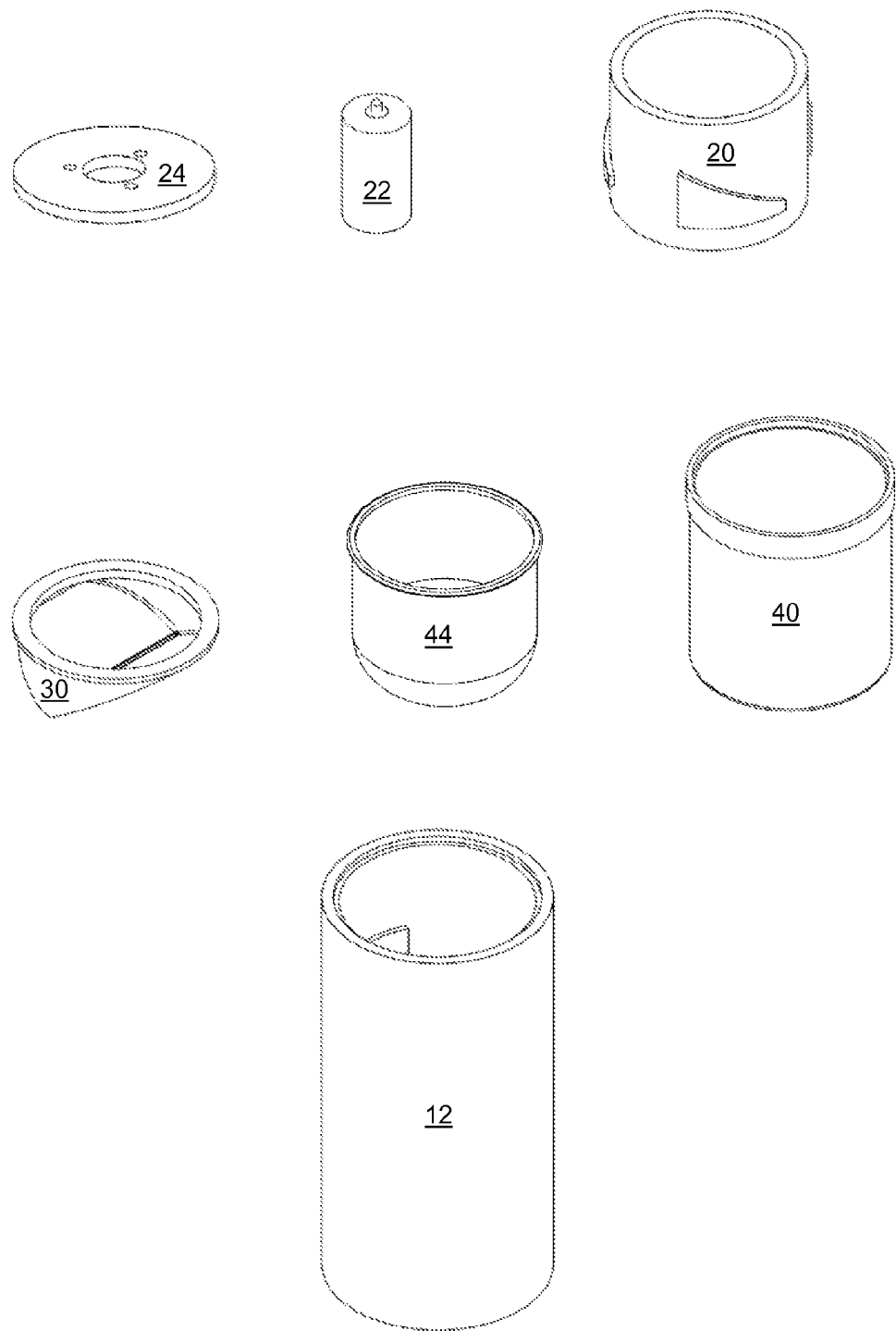
Figure 4:
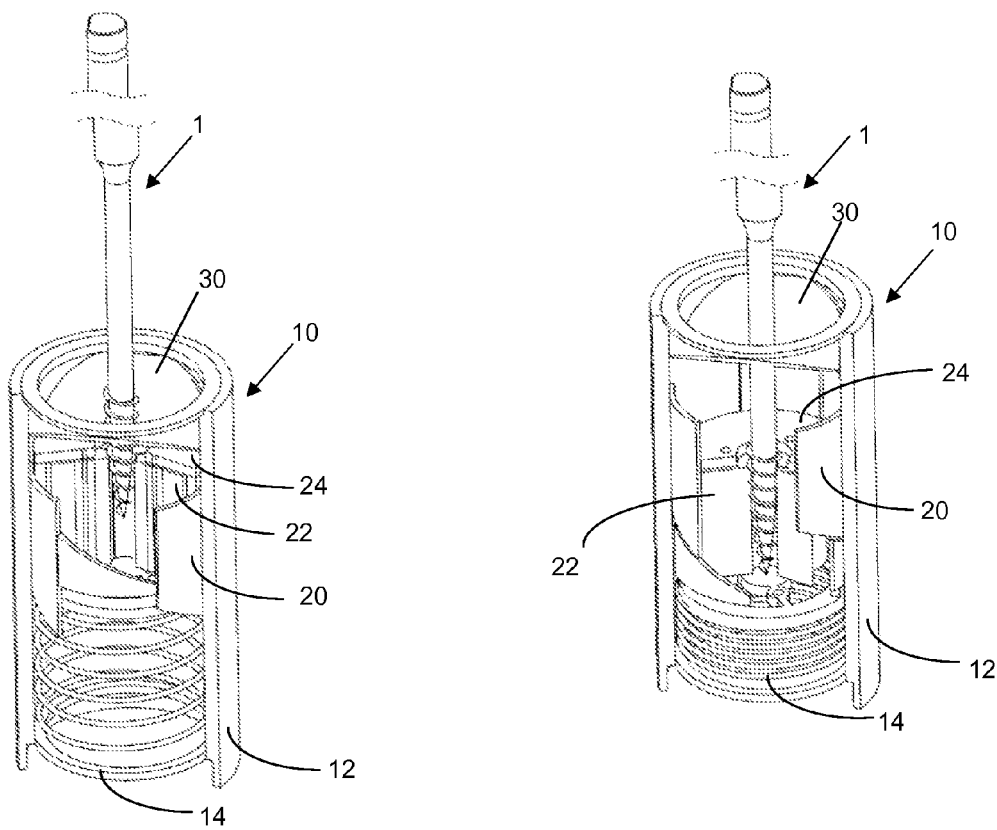
Figure 7:
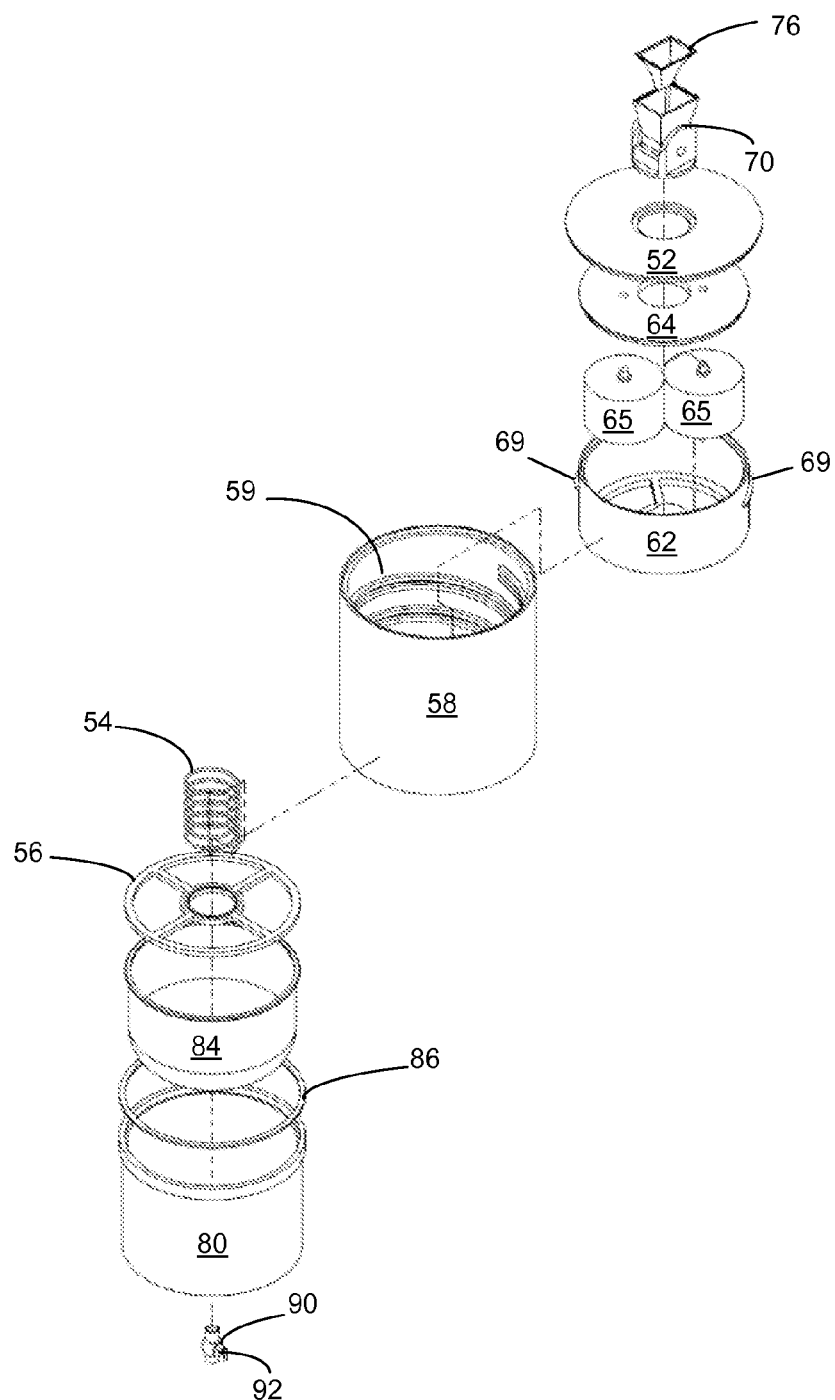
Figure 8:
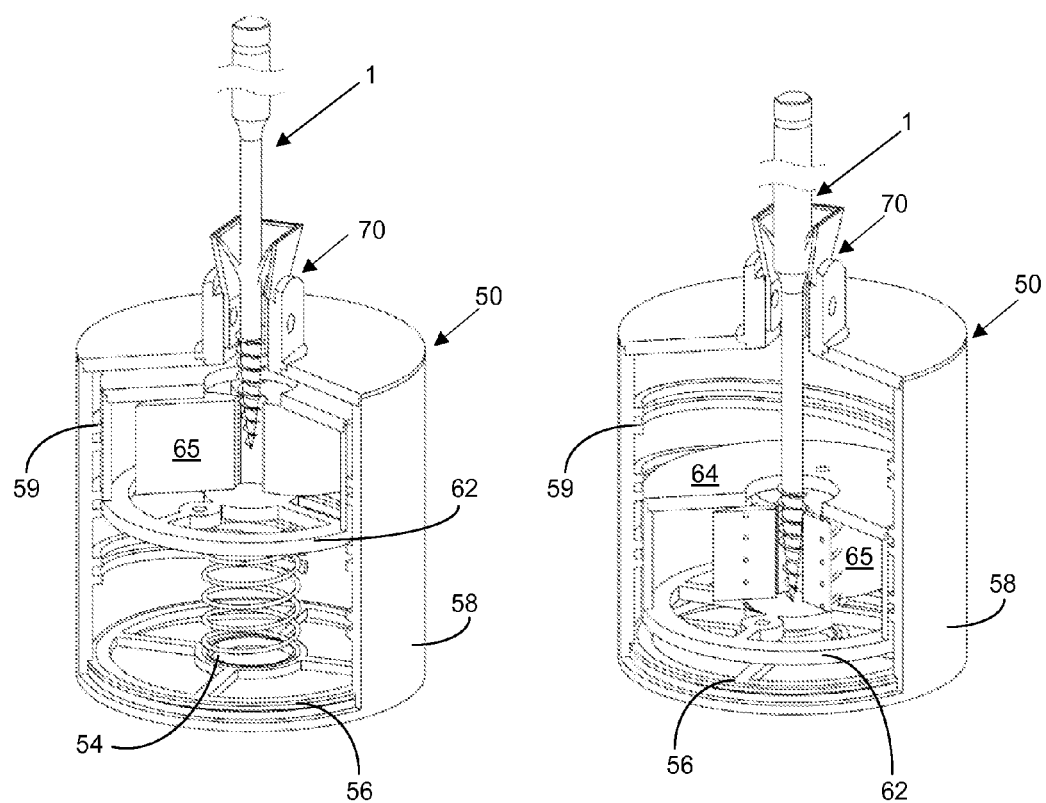
Figure 9:
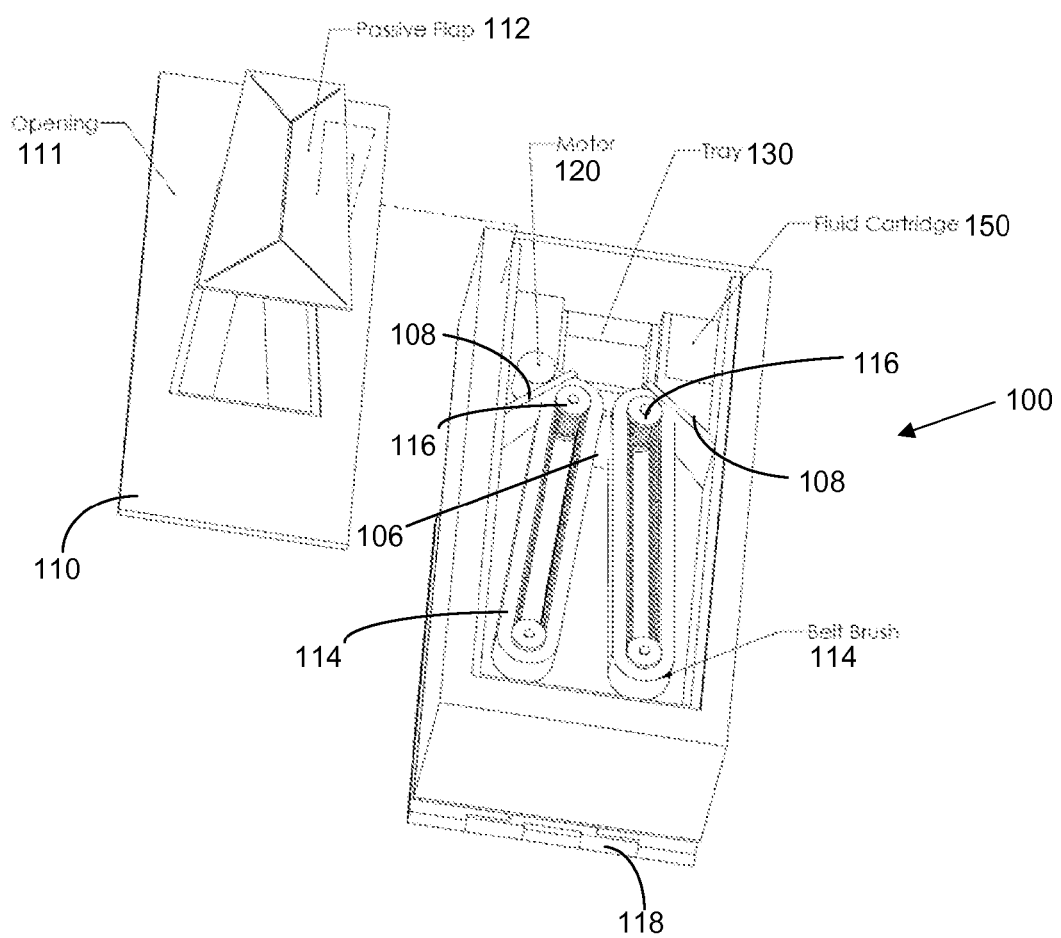
Figure 10:
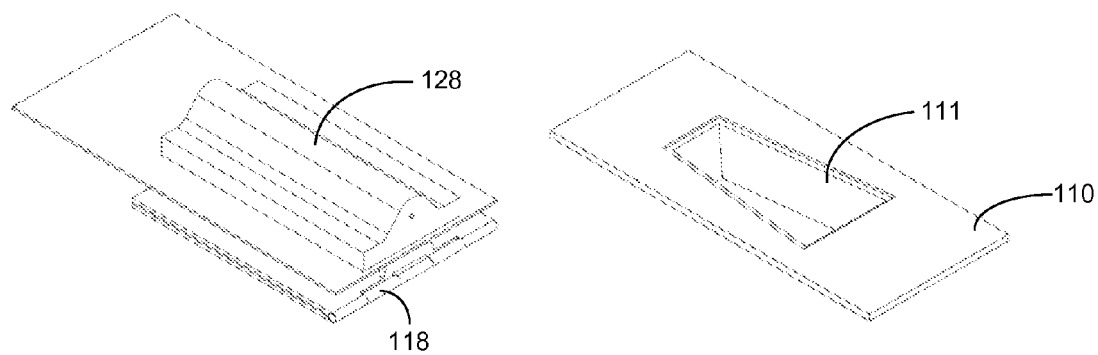
Figure 11:
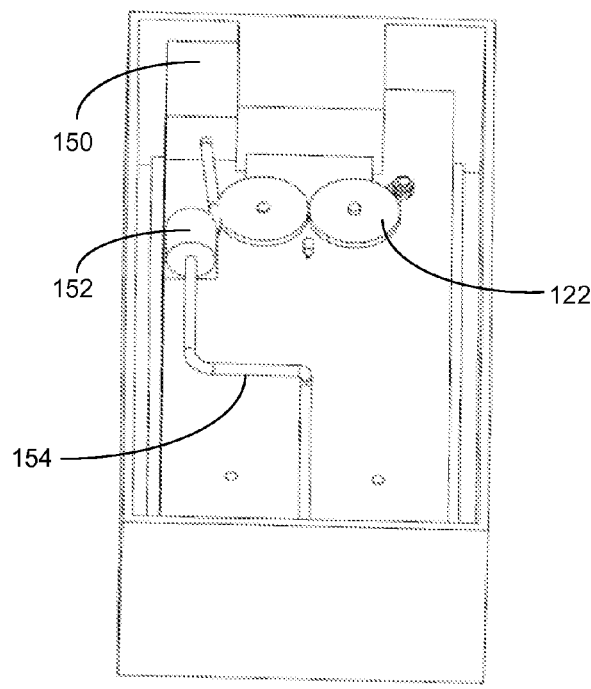
Figure 15:
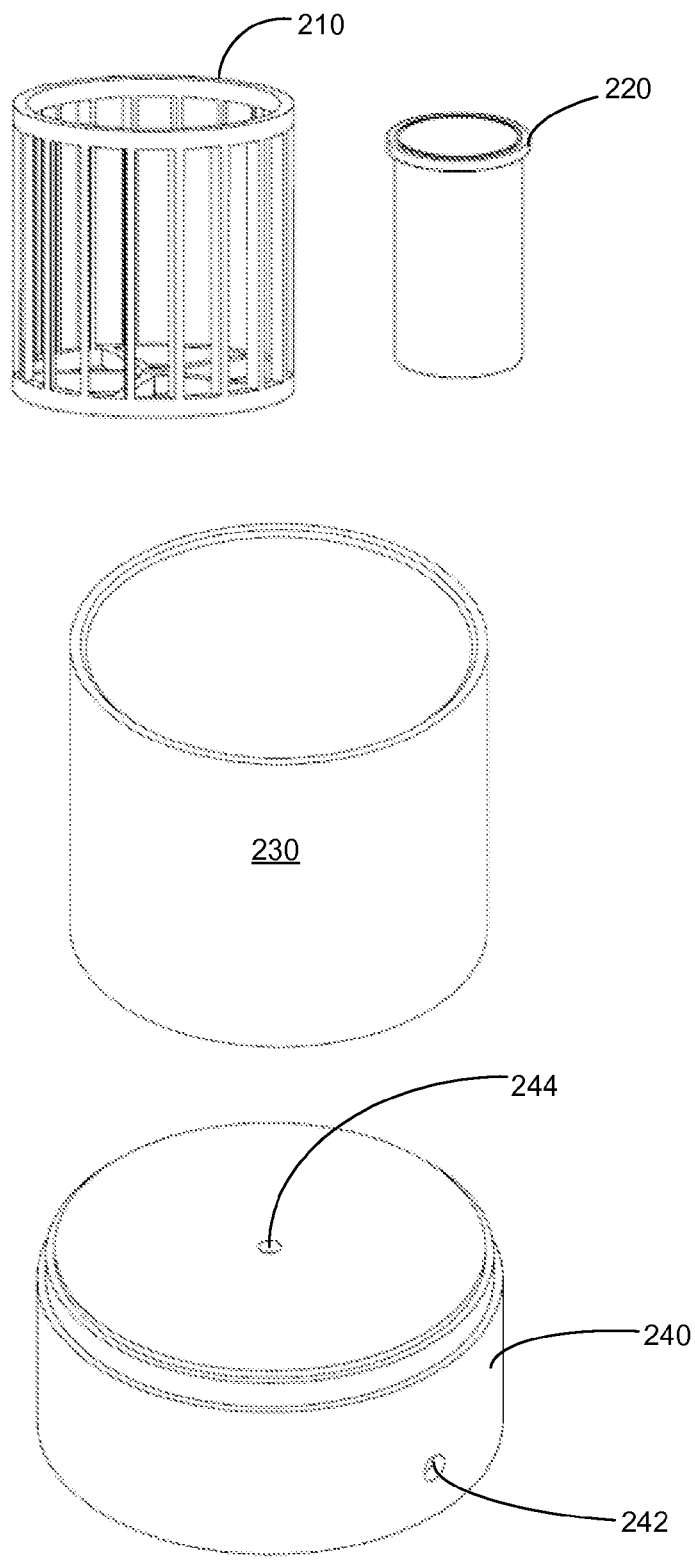
Figure 16:
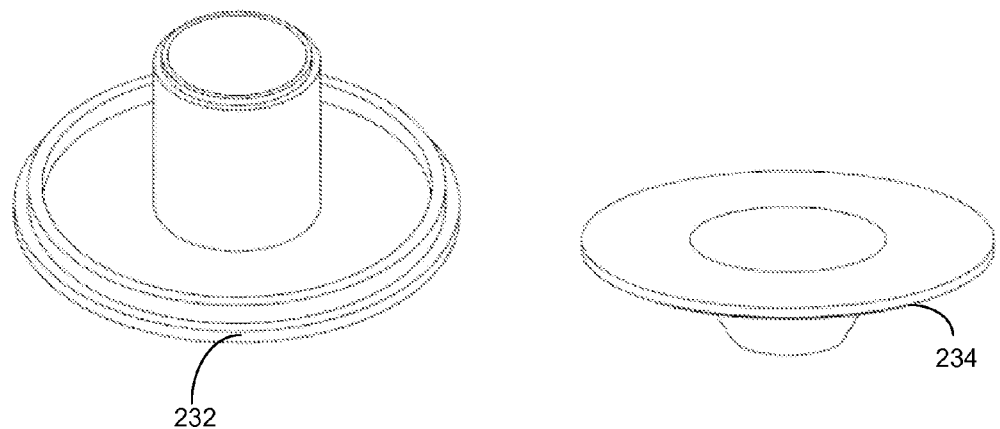
Figure 17:
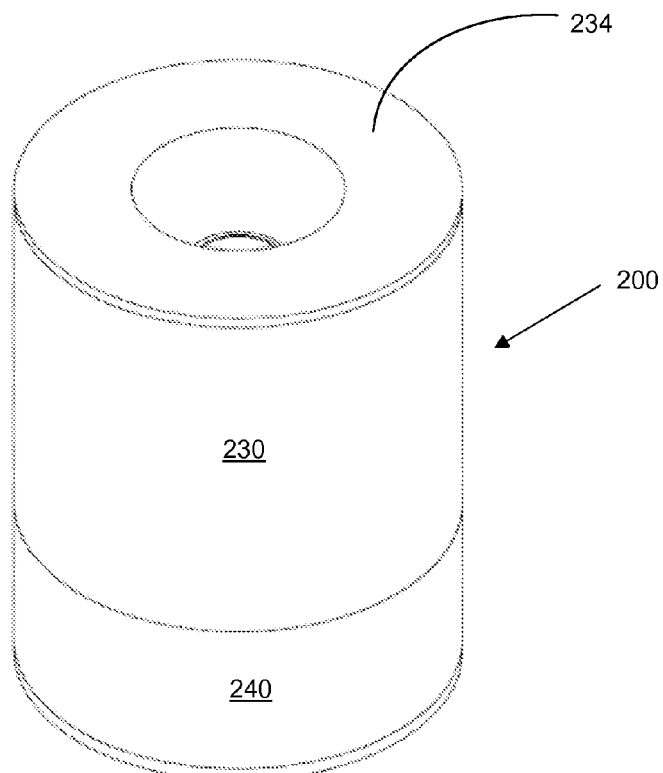
Figure 18:
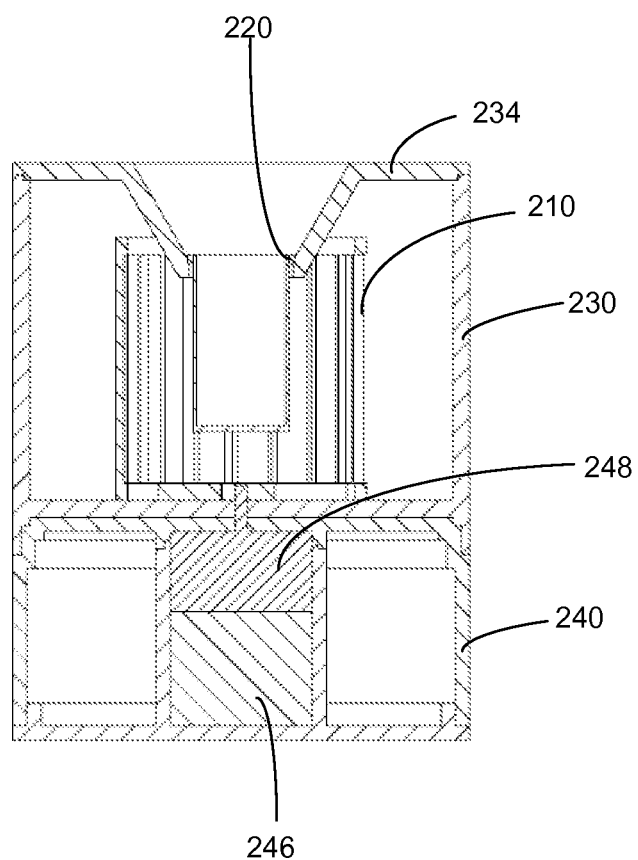
Figure 19:
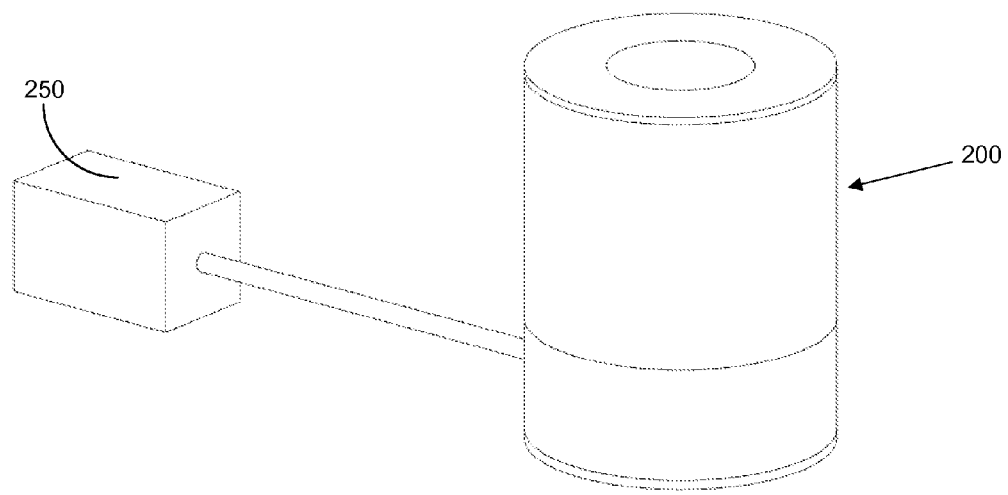
Figure 20:
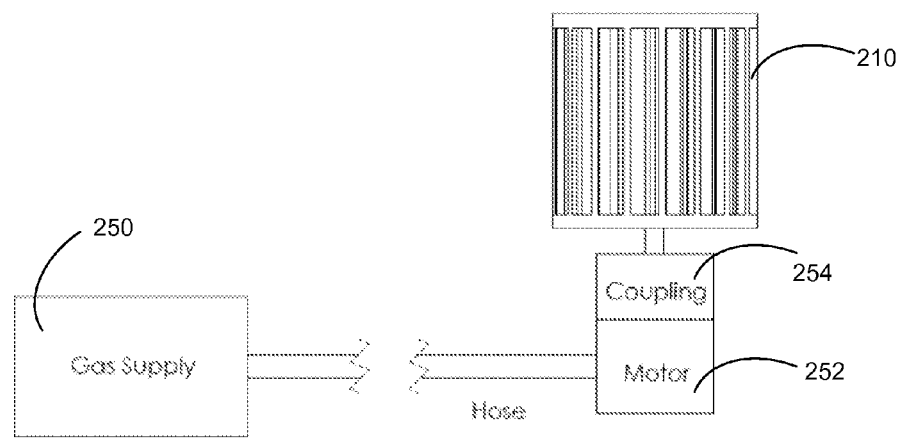

FIG. 3 includes several perspective views of components used with the apparatus shown in FIG. 1;

FIG. 4 includes two partial sectional views of the apparatus shown in FIG. 1 in two positions of use;

FIG. 5 is a perspective view of a cleaning apparatus according to one alternative embodiment of the present disclosure;

FIG. 6 includes perspective views of components used with the apparatus shown in FIG. 5;

FIG. 7 is an exploded view of the apparatus shown in FIG. 5;

FIG. 8 includes two partial sectional views of the apparatus shown in FIG. 5 in two positions of use;

FIG. 9 is a perspective view of a cleaning apparatus according to one embodiment of the present disclosure;

FIG. 10 includes perspective views of the adjustable base and cover for the apparatus shown in FIG. 9;

FIG. 11 is a top perspective sectional view of the apparatus shown in FIG. 9 with the cleaning brushes removed;

FIG. 12 includes a another perspective and a detailed view of a cleaning apparatus according to an alternate embodiment of the present disclosure;

FIG. 13 is a top plan view of the base of the apparatus shown in FIG. 12;

FIG. 14 is a detailed view of the apparatus shown in FIG. 13;

FIG. 15 includes perspective views of a cleaning apparatus according to one embodiment of the present disclosure;

FIG. 16 includes perspective views of components used with the apparatus shown in FIG. 15;

FIG. 17 is a front perspective view of the cleaning apparatus shown in FIG. 15;

FIG. 18 is a sectional view of the apparatus shown in FIG. 15;

FIG. 19 is a perspective view of the apparatus shown in FIG. 15 according to one alternative embodiment, wherein the apparatus is pneumatically driven;

FIG. 20 is a schematic view of the apparatus shown in FIG. 19; and

Figure 21:
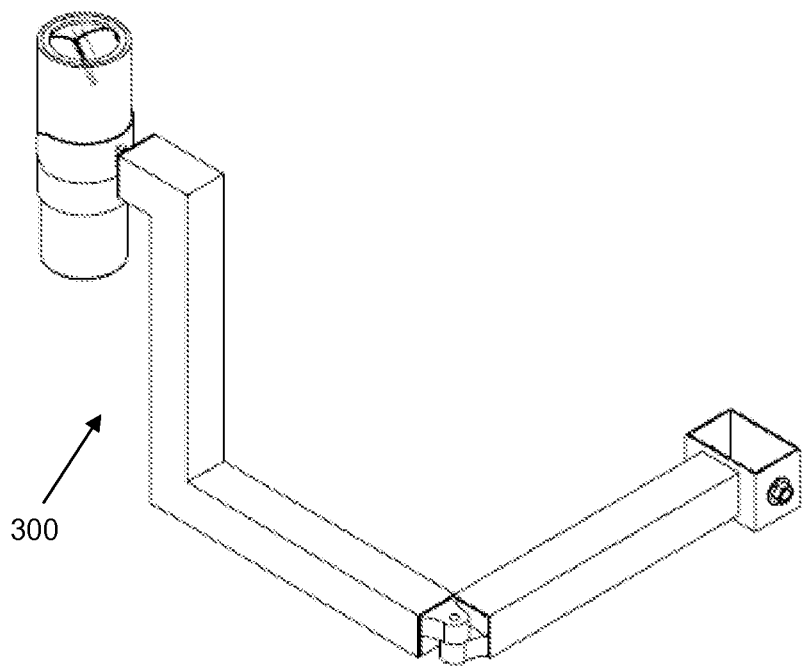

FIG. 21 is a perspective view of one coupling mechanism for attaching a cleaning apparatus to an operating table.

DETAILED DESCRIPTION

As shown in the appended FIGS. 1-21 and described in further detail herein, the present disclosure relates to a cleaning apparatus that has the ability to clean a variety of instruments and instrument types, and may provide a combination of removal and collection of certain material(s) from one or more surgical instruments. The cleaning apparatus may be a dry cleaning process or offered in conjunction with a saline or sterile liquid solution. In one embodiment, the cleaning apparatus continuously purges blood, bone and other debris quickly and efficiently, and may further comprise a vacuum pump or certifuge to facilitate the removal and purging of debris from an instrument.

According to various embodiments described herein, the present disclosure further relates to a cleaning apparatus which preferably comprises one or more manually, electronically or pneumatically operated cleaning elements disposed in a receiving area of the cleaning apparatus which are preferably oriented to contact and thereby clean a wide variety of instruments or tools used by surgeons and other surgical professionals. In some embodiments, the one or more cleaning elements are operated manually. In another embodiment, they are operated by a sensor that detects the presence of an instrument to be cleaned. For example, a proximity or photoelectric sensor may be utilized to detect the presence of an instrument, which is typically made from a metal or metal alloy.

Several preferred embodiments of the cleaning apparatus are shown in FIGS. 1-21. According to the device depicted in the Figures, one aspect of the present disclosure is that the cleaning apparatus provides means for containing, ingesting and/or collecting whatever material/debris is attached to or has been retrieved by the instrument. In one embodiment, the cleaning mechanism comprises multiple compartments or zones to permit this containment, ingesting, segregation and collection to occur.

According to one embodiment, the cleaning apparatus comprises a collection tray or compartment that may be removed easily and the material contained therein processed. For example, material captured by the collection tray may include one or more types of bone, which may be processed for use in a subsequent surgical procedure or in some embodiments in the same procedure as the one in which the bone was obtained. The collected bone material may be used, for example, in a surgical fusion procedure as bone graft. In one embodiment, the cleaning apparatus further comprises a bath of chemical solution to continuously clean and sterilize the bone or other reusable materials collected by the cleaning apparatus until those materials are retrieved by the surgeon or other medical professional for reuse.

In a preferred embodiment, the cleaning apparatus houses at least one brush for removing material from the instrument to be cleaned, and may comprise a plurality of brushes. Brushes may be fine or coarse brushes, depending on the instruments to be cleaned, and at least in some embodiments may be removable and replaceable depending on the application and the type of surgical procedure (and hence, the type of instruments that are going to be utilized in that surgical procedure). In one embodiment, the brushes are disposable. Brushes are preferably rotational brushes, but may alternatively be belt driven brushes and may be grooved, and which are coupled to a motor or other power source for supplying the rotational or translational force needed to move the brushes when an instrument is present inside the housing. In one embodiment, the motor is activated by a relay or solid state motor starter, which in turn is activated by a sensor, such as a proximity or photoelectric sensor, which detects the presence of an instrument inside the housing and signals the motor to rotate the brushes.

In one embodiment, the cleaning apparatus also houses a fluid reservoir, which may reside adjacent to the brushes. In one embodiment, the reservoir is connected to one or more fluid injection ports, which are oriented to distribute fluid from the reservoir to the surface of the brushes to lubricate the brushes and/or the surfaces of the instruments. In a preferred embodiment, the sensor which triggers rotation of the brushes also signals a pump located in the reservoir to distribute approximately 5 to 50 cc of saline solution, for example, to the fluid injection ports to lubricate the brushes prior to, and/or during the cleaning operation. In an alternative embodiment, the brushes are positioned to at least partially become submerged in the fluid reservoir, so that during their rotation the brushes pass through the fluid in the reservoir and lubricate in this manner. Although saline is used here by way of example, it is expressly understood that other fluid maybe suitable for use with the cleaning apparatus without departing from the novel aspects of the present disclosure.

Referring now in particular to FIGS. 1-4, one embodiment of the present disclosure is shown. According to this embodiment, a cleaning apparatus 10 is manually operated and permits, for example, a single instrument to be inserted linearly into the cleaning apparatus 10 by inserting the instrument into an entry valve 30. As used herein, the term "entry valve" refers to an entry port or access port through which the user inserts the instrument or other device to be cleaned into the internal cleaning portion or chamber of the cleaning apparatus 10. The entry valve 30 may be an opening of a specific geometric shape, for example, but not limited to, a circular, oval, square, rectangular, cross-shaped or any other suitable shape sized to allow insertion of the device being cleaned into the cleaning portion of the device. In further embodiments of the present invention, the entry valve 30 may comprise a cover over the valve opening.

In some embodiments of the present invention, the entry valve 30 may comprise a cover constructed from a flexible, pliable, conformable, or bendable material with a hole or slot passing through the cover, to allow an instrument to be inserted therethrough. The cover may be sized to substantially cover the entire open surface area of the entry valve opening. For example, a flexible slotted cover will keep the internal components of the cleaning apparatus at least somewhat isolated from the outside environment when the apparatus 10 is not in use. However, when the user is ready to clean in instrument, the flexible slotted cover will reversibly open to allow the instrument to be inserted through the cover and the entry port, into the cleaning portion of the cleaning apparatus 10. In some embodiments of the present invention, a hole or slot in a flexible cover may flexibly and reversibly mold around the instrument that has been inserted therethrough to provide a liquid-tight seal. When the user is finished cleaning the device, the hole or slot in the flexible cover allows the user to easily withdraw the instrument, and then the hole or slot in the flexible cover reseals to isolate the apparatus' internal components from the outside environment. An entry valve 30 cover may be constructed from any suitably flexible and moldable plastic material.

In some embodiments of the present invention, the entry valve 30 may be an opening placed in the center of a circular planar structure that is built into or attached to the top end of a circular body 12. In a preferred embodiment of the present invention, the entry valve 30 may comprise a circular funnel-shaped structure in which the lower internal portion of the funnel-shaped structure terminates with a rectangular-shaped, or slotted, opening. In such an embodiment, the funnel-shaped structure comprises two opposing, angled planar structures, which nearly intersect at the bottom of the funnel structure, but instead terminate just before intersection, to leave a gap that forms the rectangular opening at the bottom of the funnel. As used herein, such an entry valve 30 with a funnel terminating with a slotted opening may be referred to as a "duck bill" entry valve.

In further embodiments of the present invention, the entry valve 30 may further comprise a circular shaped funnel that terminates with a circular or oval opening. A benefit of the an entry valve 30 comprising a funnel shaped structure located above the access or entry port into the internal cleaning structures of the cleaning apparatus 10 is that the funnel will assist the user with guiding the instrument into the cleaning apparatus 10. The funnel shape is especially beneficial in cases where the user must maintain visual focus away from the cleaning apparatus 10, e.g. on a delicate surgical procedure, but still needs to quickly insert the medical device for cleaning. The combination of the duck bill entry valve 30 and the funnel structure results in the user only needing to position the device to be cleaned inside the large open area of the funnel, and subsequent insertion, cleaning and withdrawal of the device may be easily accomplished by touch.

In addition, a funnel-structure integrated into the entry valve 30 facilitates a cleaner operation of the cleaning apparatus 10, in that blood, bone, and/or tissue on the device being cleaned will tend to be directed into the cleaning apparatus 10, instead of on to the floor, table, or surrounding areas. This will facilitate better recovery of these materials, and provide better sterility among other instruments and apparatus in the work area.

In some embodiments of the present invention, the entry valve 30 may comprise threads that may allow a screw attachment with receiving threads on the body 12. In further embodiments, the entry valve 30 may comprise a snap attachment, which physically couples to a receiving snap attachment built into the body 12. In still further embodiments, the outer circumference of the entry valve 30 may sit inside a ledge built into the top end of the body 12, wherein the entry valve 30 is held flush against the body by gravity. In a further embodiment of the present invention, the entry valve 30 comprises a circular opening positioned at the narrow, terminal end of a funnel structure, wherein the top wide portion of the funnel structure provides threads around the outside circumference of the wide funnel structure, such that the threads mate with corresponding threads located at the top end, on the inside wall of the body 12.

Referring now to FIGS. 2 and 3, the body 12 preferably provides a housing for at least one brush cartridge 20 and at least one biasing member or spring 14; e.g. the brush cartridge 20 and spring 14 are located inside a hollow body 12. In some embodiments of the present invention, the body 12 comprises a cylinder comprising a top end, a bottom end, and a length spanning between the two ends. The length may comprise a constant cross-sectional area for the entire length of the cylinder. The top end of the body 12 preferably receives the entry valve 30, e.g. the duckbill entry valve, and may be threaded to receive threads located on the entry valve 30. Threads may be located on the inside wall of a cylindrical body 12, or on the outside wall of a cylindrical body 12. The bottom end of the body 12 may receive a collection or specimen jar 40. In preferred embodiments of the present invention, the bottom end of the body 12 may be threaded to receive threads on the specimen jar 40, to allow the easy attachment and detachment of the specimen jar 40 to the bottom end of the body 12.

In further embodiments of the present invention, the body 12 may comprise a lip or ledge located on the top end of the body 12, which is constructed to receive the outside circumference of the entry valve 30. In still further embodiments of the present invention, the inside wall of the body 12 may contain a slot positioned near the top end of the body 12 for receiving an o-ring, gasket, or seal. Placement of the entry valve 30 into the top end of the body 12 may then facilitate compression of the o-ring, gasket, or seal between the inside wall of the body 12 and the outside circumference of the entry valve 30 to make a liquid-tight seal. In still further embodiments of the present invention, the inside wall of the body 12 may contain a slot positioned near the bottom end of the body 12 for receiving an o-ring, gasket, or seal. Placement of the specimen jar 40 into the bottom end of the body 12 may then facilitate compression of the o-ring, gasket, or seal between in the inside wall of the body 12 and the outside circumference of the specimen jar 40 to make a liquid-tight seal.

In some embodiments of the present invention, the body 12 may comprise a means for engaging and rotating the brush cartridge 20. A means for engaging and rotating may comprise any structure or structures for slidably and reversibly connecting the inside wall of the body 12 with the outside wall of the brush cartridge 20, such that the mechanical connection allows the brush cartridge 20 to move reversibly in either direction along the longitudinal axis of the body 12, as well as allowing the brush cartridge 20 to rotate around the longitudinal axis of the body 12. As used herein, the term "reversibly" used in context with the brush cartridge 20, refers to the brush cartridge 20 being capable of moving both up and down along the longitudinal axis of the body 12.

In some embodiments of the present invention, the means for engaging and rotating the brush cartridge 20 may comprise a first structure comprising at least one recess, slot, groove, or channel, which may be integrally constructed into the inside wall of the body, wherein the first structure extends in a spiral fashion around the inside wall of the body 12, for at least a portion of the length of the body 12. Further illustration of this concept is provided in relation to FIGS. 7-8 below. As used herein, "pitch" refers to the number of complete rotations of a slot, groove, or channel, per unit length of the body. The means for engaging and rotating further comprises a second structure comprising at least one of a thread, projection, tab, extension, or other suitable structure, physically attached or integrally formed onto the outside wall of the brush cartridge 20, such that the second structure slidably and reversibly fits into the first structure.

Alternatively, the means for engaging and rotating the brush cartridge 20 may comprise a first structure comprising at least one thread, ridge, rib, spine, or other suitably constructed linear prominence, which may be integrally constructed into the inside wall of the body 12, wherein the first structure extends in a spiral or helical fashion around the inside wall of the body 12, for at least a portion of the length of the body 12. In this case, the means for engaging and rotating further comprises a second structure comprising at least one recess, slot, groove, or channel, or other suitable structure, physically attached or integrally formed onto the outside wall of the brush cartridge 20, such that the second structure fits around, within and/or couples to the first structure.

As a result of these physical relationships between the first and second structures of the means for engaging and rotating, movement of the brush cartridge 20 along the longitudinal axis of the body 12 results in the second structure, and the brush cartridge 20, to move along the first structure track mounted to the inside wall of the body. This longitudinal movement causes rotation of the brush cartridge 20 around the longitudinal axis of the body 12, and thus causes rotation of one or more brushes 22 located inside the brush cartridge 20 to rotate around, and relative to, the instrument or other medical device being cleaned. The pitch of the first structure will define the number of rotations that the brush cartridge 20 provides for per unit length of travel along the longitudinal axis.

In still further embodiments of the present invention, at least one of the first structure and second structure of the means for engaging and rotating the brush cartridge 20 within the cleaning apparatus body 12 may comprise a means for reducing friction between the first and second structures. Examples of a means for reducing friction between the first and second structures include, but are not limited to, bearings, ball bearings, rollers, wheels, non-stick surfaces, lubricant, and any other suitable structure, device or composition for reducing friction.

As one skilled in the art will recognize, the need for a means for reducing friction will depend greatly on the pitch selected for the first structure for engaging and rotating the brush cartridge 20. In other words, if a large number of rotations of the brush cartridge 20 are desired, the "track" defined by the first structure formed on the inside wall of the body, will have a small angle relative to the longitudinal axis of the body 12. This will result in a larger minimum force to move the brush cartridge 20 within the body 12, which may benefit from the use of bearings positioned with the "track." Conversely, fewer rotations of the brush cartridge 20 will result in a track with a relatively large angle relative to the longitudinal axis of the body 12, resulting in a smaller minimum force to move the brush cartridge 20 within the body 12, in which case a means for reducing friction may not be beneficial.

In still further embodiments of the present invention, the means for engaging and rotating the brush cartridge 20 may comprise at least one locating feature attached to the inside wall of the body 12, which physically engages at least one matching locating feature mounted to the outside wall of the brush cartridge 20. The at least one locating feature of the body 12 may comprise a surface extending from the inside wall of the body 12, the surface comprising at least an angled bottom edge and a tapered top edge. Similarly, the at least one located feature of the brush cartridge 20 may also comprise a surface extending from the outside wall of the brush cartridge 20, wherein this second surface comprises at least an angled top edge and a tapered bottom edge. The two angled edges are configured such that that they are angled to the same degree and in the same direction.

Thus, in operation, when the user forces the brush cartridge 20 down into the body, in the longitudinal direction, the bottom tapered edge of the brush cartridge 20 slides over the top tapered edge of the body 12. The brush cartridge 20 advances downward until the bottom end of the cylinder and/or the spring 14 prevents further movement in the longitudinal direction. Once the user removes the force used to push the brush cartridge 20 down, the spring 14 starts to move the brush cartridge 20 back to its original top position, however, now the top angled edge of the brush cylinder 20 impinges against the bottom angled edge of the cleaning apparatus body 12, preventing the two surfaces from sliding across each other in the longitudinal direction. Instead, the two opposing angled edges slide against each other, resulting in rotational movement of the brush cartridge 20 around the longitudinal axis of the body 12 as best shown in FIG. 4. The first and second surfaces may also both comprise a corresponding width. The combination of these widths and the angle of the angled edges will define the number of rotations achievable by the brush cartridge 20 as the spring 14 advances it back to the top starting position.

Other possible embodiments of the present invention for a means for engaging and rotating the brush cylinder are incorporated herein by reference in their entirety, for enablement purposes, including U.S. Pat. Nos. 7,982,885, 7,518,598, 6,908,247, and 6,745,424, U.S. Patent Application Publication No. 2013/0055514 and PCT Patent Application Publication Nos. WO 2013/076026 and WO 2009/091709.

A biasing member or spring 14 is preferably positioned within the body 12 of the cleaning apparatus 10, between the brush cartridge 20 and the specimen jar 40. As one of ordinary skill in the art will recognize, the spring 14 is preferably selected to provide a force sufficient to return the brush cartridge 20 from a bottom position located at the bottom end of the body 12 to a loading position wherein the brush cartridge 20 is located at the top end of the body 12. However, a balance will be made such that the spring 14 is not designed to be so stiff as to require the user to apply excessive force to push the brush cartridge 20 downward. In some embodiments of the present invention, at least one spring 14 is positioned between the brush cartridge 20 and the specimen jar 40. A spring 14 used in some of the embodiments may comprise at least one coil spring, flat spring, helical spring, leaf spring, or any other suitable spring. In some embodiments of the present invention, the cleaning apparatus 10 may comprise at least one spring 14 comprising a compression spring, a constant spring, and a variable spring.

In some embodiments of the present invention, the cleaning apparatus 10 may comprise a torsion spring, either alone or in combination with the means for engaging and rotating the brush cartridge. As used herein, a "torsion spring" is a spring that provides a torque or twisting force such that the end of spring rotates through an angle is a load is applied (or released).

In some embodiments of the present invention, a coil spring (or multiple springs) 14 may be selected with an outside diameter sized such that the coil spring 14 is positioned inside the apparatus body, against the inside wall of the body. A small gap may be provided between the spring 14 in the inside wall of the body 12, to allow the coil spring 14 to function properly during compression and extension of the spring 14. Such a gap will also be large enough to avoid accidental contact of the spring 14 with the first structure of the means for engaging and rotating the brush cartridge 20. The coil spring 14 may further comprise a top end and a bottom end, wherein the top end of the coil spring 14 abuts against the bottom surface of the brush cartridge 20. The bottom end of the coil spring 14 may be constructed to rest on top of a surface extending radially outward from the inside wall of the body 12, or alternatively, the bottom end of the spring 14 may rest on a portion of the top surface of the specimen jar 40. Sizing a coil spring 14 to have an outside diameter as close as reasonably possible to the inside diameter of the brush cartridge 20 will assist with maintaining the shape and spring force generated by the coil spring 14 is it is compressed and released.

In further embodiments of the present invention, the spring 14 may comprise a spring with an outside diameter substantially less than the inside diameter of the body 12. Such a spring design will eliminate potential unwanted physical rubbing between the outside diameter of the spring 14 and the first structure of the means for engaging and rotating the brush cartridge 20; e.g. spring contact with a ridge, thread, notch, etc. The top end of a spring 14 with a small diameter relative to the body 12 diameter may be physically attached to, and abut against, the bottom surface of the brush cartridge 20 to assist with maintaining the vertical alignment of the spring 14, relative to the longitudinal axis of the body 12. In still further embodiments of the present invention, the bottom end of the spring 14 may be physically attached to a portion of the top surface of the specimen jar 40. For example, a bridge may extend across the top surface of the specimen jar 40, providing a surface for the spring 14 to impinge against, providing a stopping barrier to allow the spring 14 to be compressed. Similarly, such a bridge may extend across the bottom end of the body 12.

It is desirable to select a spring 14 whose cross-sectional area is small relative to the cross-sectional area of the cleaning apparatus body 12. This is because it is desirable to maintain as much of the internal volume of the body 12 as possible in an empty state, so that debris (e.g. bone matter, tissue, etc.) may fall unhindered into the specimen jar 40. This point also illustrates that it may be desirable to select a spring 14 with as small an outside diameter as is reasonable, and with as few coils as is possible.

Alternatively to a spring 14, some embodiments of the present invention may incorporate a piston or other type of biasing member, wherein the at least one biasing member is placed within a cylindrical housing. A piston may provide the advantage of virtually eliminating surfaces on which debris removed from the instrument being cleaned can collect. A piston may also facilitate easier cleaning between uses. In still further embodiments, a piston may comprise some other reversibly compressible element other than a spring; e.g. an elastomere, a fluid, a gas, etc.

At least one filter 44 is preferably positioned substantially within the specimen jar 40. In some embodiments of the present invention, a filter 44 may comprise an outside cylindrical wall and an open top face. The open top face allows both liquid and solid particulate to settle by gravity from the brush cartridge 20 exit into the internal volume formed by the filter 44 cylindrical wall. The filter 44 further comprises a closed bottom face. The bottom face may comprise a mesh, filter or screen material, wherein liquid and fine particles can pass through the bottom face. However, larger particles are retained within the volume formed by the filter 44. The hole size and shape of the filter 44 may be sized and selected for a particular application. For example, a bottom face comprising a stainless steel mesh may be selected with a Tyler mesh size of 80, which will capture all particles with an average diameter of greater than 0.180 mm. Alternatively, a bottom face may be selected to capture finer particles; e.g. a Tyler mesh size of 325 corresponding to allowing all particles smaller than 0.045 mm to pass through the filter. Multiple filters 44 may be used in series, as needed for a particular application. In some embodiments, multiple filters 44 are stacked inside of each other, to provide a series of filtration steps to the liquid passing through the cleaning apparatus 10.

In some embodiments of the present invention, the generally cylindrical wall of the filter 44 may also be constructed of a mesh, filter, or screen material, wherein liquid and fine particles can pass through the cylindrical wall. This may be desirable for application where the user is generating relatively large amounts of debris, such that the bottom face becomes completely covered with debris and the holes within the mesh, filter, or screen become occluded and can no longer pass liquid. In this situation, a cylindrical wall comprising a mesh, filter, or screen material will provide additional surface area for "filtration" and may enable the user to perform longer procedures without the need to empty the filter 44.

In some embodiments of the present invention, the filter 44 is designed to be autoclaved and reused. Therefore, the filter 44 (as well as any of the other components of the apparatus for cleaning) may be constructed from materials that are suitable for typical autoclaving conditions (121-123° C. at 15 psig for at least 30 minutes). Suitable materials of construction for autoclaving include, but are not limited, to stainless steel, borosilicate glass, polypropylene, and polycarbonate.

In other embodiments of the present disclosure, the filter 44 is disposable. In other embodiments, the filter is substantially disc shaped and does not reside substantially within the specimen jar 40, but rather resides immediately adjacent and above the specimen jar 40.

In preferred embodiments of the present invention, a specimen jar 40 is provided. A specimen jar 40 provides an internal volume preferably to house the filter 44, in which the material removed from the instrument is collected. In some embodiments of the present invention, a specimen jar 40 may be an extension of the body 12, wherein the specimen jar 40 and body 12 are one piece and the specimen jar 40 is positioned below the spring 14 and the brush cartridge 20. In other words, in some embodiments of the present invention, the body 12 of the cleaning apparatus 10 is a single piece that houses the brush cartridge 20, the spring 14, and the filter 44, and is capped on the top end by an entry valve 30, and is capped on the bottom end with a means for draining the body.

In some further embodiments of the present invention, a specimen jar 40 may be a separate and independent element of the cleaning apparatus 10, wherein the specimen jar 40 may be attached and detached from the bottom end of the body 12. A specimen jar 40 may comprise a hollow cylindrical sidewall further comprising a length, an inside diameter, and an outside diameter. In some embodiments the sidewall of the specimen jar 40 may comprise an inside diameter and outside diameter that are substantially equal to the inside and outside diameters of the body, respectively. The top end of the specimen jar 40 may comprise a substantially open surface area, to allow solids and liquids to freely flow and settle from the body 12 into the internal volume of the specimen jar 40.

In still further embodiments of the present invention, the top end of the specimen jar 40 reversibly interconnects with the bottom end of the body 12, utilizing a means for connecting. A means for connecting may comprise at least one of mating threads, or any other suitable quick-disconnecting attachments known to one of ordinary skill in the art. Further, the top end of the specimen jar 40 may provide a lip, ledge, or recess, etc. that is configured to receive an o-ring, gasket, or seal such that placement of the specimen jar 40 into the bottom end of the body 12 may then facilitate compression of the o-ring, gasket, or seal between the inside wall of the body 12 and the outside circumference of the specimen jar 40 to make a liquid-tight seal.

In some embodiments of the present invention, the specimen jar 40 may comprise an exit port positioned within a bottom face of the specimen jar 40. An exit port incorporated into the bottom of the specimen jar 40 will facilitate removal of solids and liquid from cleaning apparatus 10. Such removal may be by passive gravity draining through the exit port, or by some active means for draining Examples of active means for draining including, applying a vacuum source to the exit port, applying a pressure to the entry valve 30 of the body 12 to force flow through the exit port, and/or applying a centrifugal force to the cleaning apparatus 10 to force flow through the exit port.

In some embodiments of the present invention, an exit port in the specimen jar 40 may simply be an opening. For example, a hose barb may be attached to the exit port, to facilitate attachment of tubing to allow liquid to drain from the cleaning apparatus 10, through the tubing, to a collection vessel. A hose barb may also be used to apply a vacuum source to the specimen jar 40. For such an embodiment, a system for cleaning an instrument may comprise the cleaning apparatus, a liquid trap, and a vacuum pump.

In still further embodiments of the present invention, the exit port may further comprise a valve, such that the valve can be opened and closed as desired by the user. As would be known to one of ordinary skill in the art, any hose barb, valve, or other desirable fitting, may be attached to the bottom end of the specimen jar by welding the fitting to the specimen jar, by use of threaded connections, compression fittings, sanitary fittings, or any other suitable connections. Further illustration of this concept is provided in relation to FIG. 7 and described below.

In some embodiments of the present invention, the specimen jar 40 does not include an exit port. In such embodiments, the specimen jar 40 may be removed from the body 12 to facilitate removal of the liquid and debris that have collected within the specimen jar 40. In some further embodiments, a lid may be provided that reversibly attaches to the open top end of the specimen jar 40. This may enable the specimen jar 40 to be placed in a centrifuge to enable more complete separation of the solids from the liquids, especially in cases where the filter 44 comprises a very fine mesh, screen, or filter material.

In some further embodiments of the present invention, the specimen jar 40 may provide a surface that physically abuts against the lower end of the spring 44, thus providing a physical stop that allows the spring 44 to be compressed when the user applies a downward force to the brush cartridge 20. In some embodiments, such a surface may be a ledge or lip that extends from the inside wall of the specimen jar 40, around the inner circumference of the specimen jar 40, wherein the inside diameter of the ledge or lip is less than the outside diameter of the spring 14. Such a ledge or lip is envisioned for embodiments wherein the spring 44 diameter is substantially equal to the inside diameter of the body 12.

Alternatively, a surface that physically abuts against the lower end of the spring 14 may comprise a bridge that extends across the diameter of the open upper end of the specimen jar 40. Such a configuration is envisioned for embodiments that employ a spring 14 with an outside diameter that is substantially smaller than the inside diameter of the body 12. In either embodiment, a bridge or a ledge or lip configured into the top end of the specimen jar 40, removal of the specimen jar 40 from the body 12 will allow both the spring 14 and the brush cartridge 20 to be removed from the body 12.

A brush cartridge 20 is preferably provided within the cleaning chamber and provides an internal volume in which the instrument is physically and/or chemically cleaned. As used herein "physical cleaning" refers to any mechanical, frictional, vibrational, and/or ultrasonic means for applying a force to the instrument being cleaned. As used herein "chemical cleaning" refers to the use of a chemical agent that affects the chemical properties of a solution stored in the brush cartridge and/or the chemical properties of the debris being cleaned from the instrument. Examples of chemical properties include, but are not limited to, solubility, miscibility, surface tension, density, and reactivity.

In some embodiments of the present invention, a brush cartridge 20 may comprise a hollow cylindrical body comprising a wall, a top end, and a bottom end. The wall may further comprise a length along the longitudinal axis of the body, an inside diameter, and an outside diameter. The outside diameter of the wall is configured such that the brush cartridge 20 physically communicates with the inside wall of the body 12 through the use of the means for engaging and rotating the brush cartridge 20. As such, the outside diameter of the brush cartridge 20 may be less than the inside diameter of the body 12.

The length of the brush cartridge 20 may comprise a length that is equal to or less than the length of the body 12. In some embodiments wherein the brush cartridge 20 length is equal to the length of the body 12, a means for engaging and rotating the brush cartridge 20, and a spring 14, are not needed, and cleaning of the instrument is provided only by the motion of inserting and retracting the instrument into the brush cartridge 20 through the entry valve 30. In such an embodiment, a separate and independent brush cartridge 20 that is inserted into the body 12 may be eliminated, wherein the cleaning elements (e.g. brushes) are physically incorporated/attached directly into the body 12.

In some embodiments of the present invention, a top end of the brush cartridge 20 may comprise a cap comprising a flat surface, or in other words a brush cartridge cover 24, and having an entry port therethrough. The entry port may be an opening sized to accept insertion of the instrument therethrough. The entry port into the brush cartridge 20 may be an opening of a specific geometric shape, for example, but not limited to, a circular, oval, square, rectangular, or any other suitable shape sized to allow insertion of the device being cleaned into the brush cartridge. According to other embodiments, the entry port comprises a second stage or level to provide further containment and cleaning of the instrument as it is removed from the entry port. In some further embodiments of the present invention, the brush cartridge entry port is substantially the same size and shape as the entry valve 30 opening positioned above it.

In some further embodiments of the present invention, the cleaning apparatus is configured such that when the brush cartridge 20 is at the top of the body 12 (e.g. when the spring is not compressed), the brush cartridge entry port is substantially aligned with the entry valve 30 opening. For example, for the case of a circular entry valve 30 opening, a circular brush cartridge entry port will be positioned directly below the circular entry valve 30 opening. For example, in the case of a rectangular entry valve 30 opening, a rectangular brush cartridge entry port will be aligned with and directly below the rectangular entry valve 30 opening. For rectangular openings, "aligned" refers to at least the long dimensions of the rectangular openings being parallel, with the rectangular openings positioned directly above or below each other. For circular openings, "aligned" refers to at least the center points of the circular openings being positioned substantially along the same longitudinal axis of the body.

In some embodiments of the present invention, the brush cartridge cover 24 on the top end of the brush cartridge 20 may comprise at least one means for attaching an instrument or other device to the brush cartridge 20 for providing physical cleaning to the instrument within the brush cartridge 20.

Referring now to FIG. 4, in some embodiments the bottom end of the brush cartridge 20 may comprise a substantially open area to allow liquid and/or debris removed from the instrument to collect in the specimen jar 40. The bottom end of the brush cartridge 20 may further comprise an impingement plate physically attached to the inside wall of the brush cartridge 20, such that the distal end of the instrument 1 physically impinges against the impingement plate when the user inserts the instrument 1 into the brush cartridge 20, thus providing the physical stop needed to push the instrument 1 and the brush cartridge 20 as a unit down into the body 12, along the longitudinal axis of the body 12. In some embodiments of the present invention, an impingement plate may comprise a circular plate, wherein the circular plate is centered within the circular cross-sectional area of the brush cartridge 20. Further, the circular plate may comprise an outside diameter that is significantly smaller than the inside diameter of the brush cartridge 20, but still large enough that the instrument 1 can impinge against the plate for a wide range of insertion angles of the instrument into the entry valve 30. At least one bridging structure may connect the impingement plate to the inside wall of the lower end of the brush cartridge 20.

In some embodiments of the present invention, a means for providing physical cleaning to an instrument may comprise at least one of a brush, a sponge, a surgical towel or fabric, a vibration mechanism, ultrasound, and any other suitable mechanical cleaning mechanism. In preferred embodiments of the present invention, a means for providing physical cleaning may comprise at least one brush 22 mounted within the internal volume of the brush cartridge 20 and physically connected therein by at least one means for attaching the at least one brush 22 to the cap and/or the bottom end of the brush cartridge 20. In some embodiments of the present invention, the means for providing physical cleaning may comprise two, three, four, five, six, or more than six brushes 22. In some further embodiments, the at least one brush 22 may comprise a length that is equal to or less than the length of the brush cartridge 20 sidewall. In still further embodiments, the at least one brush 22 is mounted within the brush cartridge 20, such that the length of the at least one brush cartridge 20 is substantially parallel to the long axis of the body 12. In still further embodiments of the present invention, the at least one brush 22 is mounted within the brush cartridge 20, such that the length of the at least one brush cartridge 20 is not substantially parallel to the long axis of the body 12. In still further embodiments of the present invention, the at least one brush 22 is mounted within the brush cartridge 20, such that the length of the at least one brush cartridge 20 is substantially perpendicular to the long axis of the body 12. In such embodiments, it will be clear to one of ordinary skill in the art, that suitable means for attaching the perpendicular brushes 22 to the inside wall of the brush cartridge 20 will be needed.

Whether to the brush cartridge 20 sidewall, the cover 24, or the brush cartridge 20 bottom end, suitable means for attaching are contemplated as would be understood to one of ordinary skill in the art, and are therefore not extensively described herein. For example, for enablement purposes, a means for attaching may comprise holes fabricated into the cap and/or bridges spanning the bottom end. In another example, each of the at least one brush may comprise a threaded fitting at the top end of its length that threads into a corresponding receiving hole located in the brush cartridge cover 24. The cover 24 is then inserted as a unit with the brushes 22 attached, into the internal volume formed by the brush cartridge 20 sidewall. Each brush 22 also comprises a stub that extends from the bottom end of the each brush 22. These stubs are then received by corresponding holes located in the bridges that span the bottom surface of the brush cartridge 20, and support the impingement plate. It should be clear to one of ordinary skill in the art that such a configuration will require a snap-fit connection between the brush cartridge cap and the brush cartridge 20 sidewall, as the physical connection of the brushes 22 with the top holes and bottom holes will hinder the rotation of the cover 24 needed to provide a threaded connection. In another example, once the brushes 22 and the cover 24 are in place, the cover 24 may be secured in place using at least one screw wherein the screw passes through the cover 24 (e.g. through a prefabricated hole) and into the sidewall of the brush cartridge 20, wherein the screw is aligned along the longitudinal axis of the body 12.

In some embodiments of the present invention, the at least one brush 22 may be fixed within the brush cartridge 20, such that the brushes 22 cannot rotate around their longitudinal axes. In further embodiments, the brushes 22 can rotate around their longitudinal axes. In still further embodiments, the brushes 22 may be spring loaded to allow flexing and force application.

In some embodiments of the present invention, the at least one brush 22 may comprise a length and a cross-sectional shape, wherein the cross-sectional shape does not change along the length of the at least one brush 22. For example, the cross-sectional shape may be circular such the brush or brushes 22 comprises cylindrical shape. Alternatively, the cross-sectional shape may be triangular, square, or any other suitable two-dimensional shape. In addition, a brush 22 cross-sectional shape may change with position along the length of the brush 22. For example, a brush 22 may comprise at least one conical section, wherein the diameter of a circular cross-section changes with length. In another example, a brush 22 comprising a triangular cross-section may rotate the triangular-cross section relative to its position along the longitudinal axis; e.g. resulting in a helical shaped brush 22.

In some embodiments of the present invention, the at least one brush 22 may be comprised of a plurality of radially extending brushes 22, which may be constructed from materials of construction comprising at least one of Nylon, Polypropylene, Polyester, Fluorinated ethylene propylene (Teflon), Polyglecaprone 25 (Monocryl), Polydioxanone (PDS), Polyglactin-910 (Vicryl), Polyglycolic acid (Dexon) or other suitable material. In still further embodiments of the present invention, the brush or brushes 22 may be constructed from materials that are suitable for autoclaving.

In some embodiments of the present invention, three brushes 22 are positioned vertically within the brush cartridge 20, wherein the outside surfaces of the brushes 22 are in physical contact with one another along each of the brushes' lengths, and the three brushes 22 form an internal space that is centered below the entry valve 30 opening and the brush cartridge 20 entry port, wherein the internal space runs the entire length of the brushes 22. In such embodiments, the instrument to be cleaned is inserted by the user through the entry valve 30, through the entry port, and into the internal space formed between the three brushes 22. As the instrument is inserted between the brushes 22, the brushes 22 provide frictional contact with the instrument, thus cleaning debris from the instrument.

Referring again to FIG. 4, when the distal end of the instrument abuts against the impingement plate, the brush cartridge 20 is forced downwards into the body along the longitudinal axis. This downward movement, causes the first and second structures of the means for engaging and rotating the brush cartridge 20 to engage one another, causing the brush cartridge 20 to rotate around the body's longitudinal axis. This rotational motion, in turn, causes the brushes 22 to move in relationship to the instrument. This rotational motion is especially effective at cleaning the instrument, especially in configurations wherein the brushes 22 are stationary within the brush cartridge 20; e.g. prohibited from rotating themselves relative to the longitudinal axis.

In some embodiments of the present invention, a chemical means for cleaning may be provided within at least one of the apparatus body, the brush cartridge, and the specimen jar. In some further embodiments of the present invention, a chemical means for cleaning the instrument, comprising a liquid is provided. In some embodiments of the present invention, a liquid may comprise at least one of water, an alcohol, an organic, a saline solution, an antiseptic, a preservative, formaldehyde, a stabilizer, an acid, a base, a solvent, and any other liquid for achieving a particular function of interest. In some further embodiments a liquid will fill all of or less than the internal empty volume of the cleaning apparatus. It should be clear to one of ordinary skill in the art, that embodiments incorporating a liquid cleaning agent will preferably incorporate o-rings, gaskets, or seals into the connections between the various elements of the cleaning apparatus: e.g. the body, the specimen jar, the entry valve, etc.

Referring now to FIGS. 5-8, an alternate embodiment of a manually operated cleaning device is shown. Although not shown, certain embodiments of the present invention may incorporate at least one motor in place of, or in addition to, the means for engaging and rotating the brush cartridge. In still further embodiments of the present invention, at least one cylindrical brush may be physically mounted lengthwise within the internal volume of the body, wherein the at least one brush is mechanically connected to a motor which is configured to cause rotational movement of the at least one brush around the axis corresponding to the length of the brush. The motor may be configured to turn on and off when specified by the user. A motor may be powered by an AC or DC current supply, provided by either a conventional wall socket and/or at least one battery.

In some embodiments of the present invention an entry port 70 into the internal volume of the cleaning apparatus 50 may comprise a hole through a lid or cap 52 on the device, wherein a first end of a flexible joint 74 is attached to the entry port, and a second end of the flexible joint 74 is connected to funnel-shaped structure 76. The flexible joint 74 is provided with a hole that passes through its entire length.

The funnel-shaped structure 76 may comprise a wide, open, mouth section, and a narrow bottom section that terminates at hole that passes through the flexible joint 74. In some embodiments of the present invention, the funnel-shaped structure 76 attached to the flexible joint 74 may comprise a "duckbill valve" as described above. The flexible joint 74 will allow the user to orient the funnel-shaped structure 76 at a desired angle to enable easier insertion of the instrument into the cleaning apparatus 50.

For example, once the flexible joint 74 is at the desired angle, the user only needs to visually place the terminal end of the instrument into the duckbill valve 76, and then can proceed by feel to insert the instrument sequentially through the duckbill valve 76, flexible joint 74, and entry point into the cleaning apparatus 50 internal volume.

An aspect of the present invention is a cleaning apparatus 50 for instruments comprising a housing 58 comprising a top surface, a bottom surface, a top end, a bottom end, and a sidewall that define an internal volume within the housing. In some embodiments of the present invention, the housing comprises a rectangular, box shape. The cleaning apparatus according to this embodiment preferably comprises a brush assembly 60 and a collection device 80. The brush assembly 60 includes a brush cartridge 62 with at least one brush 65 and a brush cartridge cover 64. A biasing member, such as a spring 54, is positioned in housing 56 between the assembly 60 and the collection device 8. Various other components are depicted in FIG. 7. The collection device 80 may include a cylindrical housing 84 and a spacer 86.

In some further embodiments of the present invention, the top surface of the housing 58 comprises an entry port, which allows the user to insert the instrument to be cleaned into the internal volume of the housing 58. The entry port may comprise a hole with any suitable geometric shape; e.g. rectangular slot, circular hole, etc. In further embodiments of the present invention, the entry port may comprise a cover over the hole. In some embodiments of the present invention, the entry port may comprise a cover constructed from a flexible, pliable, conformable, or bendable material with a hole or slot passing through the cover, to allow the instrument to be inserted therethrough. The cover may be sized to substantially cover the entire open surface area of the entry port hole. In still further embodiments the entry port may be positioned in the top end of the housing 58.

The housing may further comprise a first structure 59 as described above for connecting with a second structure 69 located relative to the brush assembly 60. The joining of the first structure 59 to the second structure 69 in this embodiment operates in the same manner described above with respect to the cleaning apparatus 10. Furthermore, the cleaning apparatus 50 may comprise an exit valve 90 which has at least two positions determined by the position of a valve handle 92 relative to the exit valve 92. Further details relating to the cleaning apparatus are also described above in relation to FIGS. 1-4 and are expressly understood to have applicability to the embodiment shown in FIGS. 5-8.

Referring now to FIGS. 9-14, in some embodiments of the present the cleaning apparatus 100 may comprise two or more counter-rotating belt brushes 114. In some embodiments a belt brush system 114 may comprise a first belt drive 116, a second belt drive 116, and a belt brush comprising a flexible planar surface comprising a width, a first end, and a second end, wherein the first and second ends are attached to one another to make a loop or "belt". As used herein, a "belt drive" is a rotatable cylinder. The belt brush system may be powered by a motor 120 of varying types and sizes.

A belt drive 116 may comprise teeth or some other suitable friction-forming surface to facilitate gripping the belt brushes 114. In some embodiments of the present invention, each first belt drive 116 may be positioned towards the top end of the housing, each equidistant from a longitudinal centerline that cuts the housing into equal parts, and wherein the rotational axes of both first belt drives 116 are perpendicular to the top surface of the housing. In addition, each second belt drive 116 may be positioned towards the bottom end of the housing, each equidistant from the longitudinal centerline that cuts the housing into equal parts, but closer together than the spacing between the two first belt drives 116, and wherein the rotational axes of both second belt drives 116 are also perpendicular to the top surface of the housing.

A belt brush 114 is then positioned around each pair of first and second belt drives 116, such that the two belt brushes 114 make a generally V-shaped formation, wherein the open end of the V is towards the top end of the housing, and the sharp end of the V is towards the bottom. Thus, there is formed between the two belt brushes 114 an interstitial space that is configured to receive the instrument that is inserted through an opening 111 in the top cover 110 of the cleaning apparatus 100. This space narrows as one moves down the length of the housing, forcing the surfaces of the two belt brushes 114 to come into contact with the distal end of the instrument being cleaned.

The angle of the V-formation may be adjusted is required to accommodate a particular instrument. In some embodiments, the angle between the two belt brushes 114 is approximately within the range of about 5° to about 25°. In still further embodiments of the present invention, a combination of elastic belt brushes 114 with moveable first drives 116 allows the user to adjust the angle between the belt brushes 114 to a desired setting.

For example, a belt drive 116 may comprise a cylinder that is rotatably coupled to an axis aligned along the longitudinal length of the cylinder. The axis may comprise a first end and a second end, wherein at least one of the ends is attached to at least one of the front surface and back surface of the housing. An axis of the cylinder may comprise, for example, a threaded end portion that extends through the front surface or back surface, to receive a washer and a wing-nut (on an outside surface of the housing; e.g. not within the housing) to allow the user to tighten the wing-nut to secure the belt drive into a desired position.

The threaded end portion of the cylinder axis may be inserted through a hole, or preferably a slot. A slot provides the ability to slide the end portion of the cylinder axis within the slot to a desired position and angle between the two belt brushes 114, at which point the wing-nut can be tightened to secure the brushes 114 at that desire position. In some embodiments of the present invention, both first belt drives 116 comprise an axis that comprise a threaded end that are both inserted through their own respective slots in the back surface, such that the angle between the corresponding belt brushes 114 can be adjusted as desired, and secured in place using a threaded wing-not, or comparable securing mechanism.

In some embodiments of the present invention, the cleaning apparatus 100 may further comprise a physical obstruction 106 placed in the interstitial space substantially centered within the sharp end of the V-formation (e.g. at the narrowest point between the two belt brushes, and towards the bottom of the housing.) The purpose of the physical obstruction 106 is to provide a tactile indication to the user that the instrument has been inserted to the maximum allowable depth in the housing. In other words, as the instrument is inserted, eventually the distal end of the instrument will impinge against the physical obstruction 106, thus preventing further insertion of the instrument.

In some embodiments of the present invention, a physical obstruction 106 may comprise a triangular wedge placed with the narrow portion of the interstitial space. A triangular wedge may further comprise a slightly convex top surface to facilitate easier gravimetric settling from the wedge to the bottom end of the housing. Alternatively, a triangular wedge may comprise a slightly concave top surface to facilitate catching the terminal end of the instrument being cleaned to prevent the belt brushes from pulling the medical device beyond the desired depth in the cleaning apparatus 100.

In some embodiments of the present invention, the cleaning apparatus 100 may comprise at least one scraper 108 that physically communicates with at least a portion of at least one belt brush 114. In some embodiments of the present invention, a scraper 108 may comprise a flat planar structure, with a lower, leading edge that is in physical contact with a belt brush. For configurations that utilize two belt brushes in a V-configuration, two scrapers 108, one for each belt brush 114, may be configured just distal to, and outside of the belt brush V-configuration, resulting in V-configured belt brushes positioned within V-configured scrapers 108. This configuration provides a mechanical shearing force for physically removing debris from the surface of the belt brushes 114.

In some embodiments of the present invention, a belt brush 114 comprises a brush surface mounted on a lower loop to form a continuous laminated belt brush. A lower loop may comprise a rubber material. The belt brush lower loop is mounted on a first belt drive 116 and a second belt drive 116 such that the lower loop, and consequentially the belt brush 114 itself, is held substantially taught between the two belt drives 116. The configuration of the belt brush 114 mounted between the two belt drives 116 results in a first portion of the brush surface that moves downwards towards the collection device.

This first portion of the brush surface reaches a lower-most position in the housing, and then rotates around a belt drive 116, resulting in a change in direction opposite to the downward motion. Thus, the belt surface comprises a second portion between the two belt drives 116 wherein the belt brush 114 moves upwards and away from the collection tray 130. In some further embodiments of the present invention, a scraper 108 is positioned in a third portion of the belt brush 114, wherein the third portion is located between the first and second portions, in the region where the belt is riding on the belt drive 116 and changing directions from a downward direction to an upward direction.

As used herein, "approach angle" refers to the angle of a planar scraper relative to a substantially flat brush surface, wherein 0 degrees refers to a planar scraper that is parallel to the brush surface, wherein the leading edge of the planar scraper is pointed in the direction that the brush surface is moving; 180 degrees refers to a planar scraper that is parallel to the brush surface, wherein the leading edge of the planar scraper is pointed in a direction opposite to the direct that brush surface is moving; and 90 degrees refers to a planar scraper this perpendicular to the brush surface. In some embodiments of the present invention, the approach angle of a planar scraper relative to a substantially flat brush surface ranges from about 90 to about 180 degrees. In still further embodiments of the present invention, the approach angle of a planar scraper ranges from about 120 to about 160 degrees.

In still further embodiments of the present invention, a debris ramp may be positioned between the at least one first belt drive and the collection tray 130. A debris ramp may comprise at least one flat planar structure that is used to divert debris that are gravimetrically removed by the at least one belt brush 114 and/or at least one scraper 108, to direct the debris into the collection tray 130. In still further embodiments of the present invention, a debris ramp may comprise two or more planar surface constructed in a funnel shape to divert and direct debris from the belt brushes 114 to the collection tray 130.

In some further embodiments of the present invention, a scraper 108 may further comprise a rectangular slot cut therethrough, wherein a portion of a belt brush 114 intersects the scraper 108 by passing through the rectangular slot.

In some embodiments of the present invention, at least both of the first belt drives and second belt drives 116 are in mechanical communication with a motor 120 which is configured to rotate the belt drives 116, which in turn causes the belt brushes 114 to move relative to the housing.

In some embodiments of the present invention, the cleaning apparatus may comprise a collection tray 130 positioned below the narrow end of the belt brush V-configuration, such that any debris and material removed from the instrument fall by gravity and are collected in the collection tray 130. In some embodiments of the present invention, a collection tray may comprise a box- or tray-like structure with an open top, through which the debris fall. In still further embodiments of the present invention, the housing of the cleaning apparatus 100 comprises a slot, receptacle, or port that allows the user to insert and remove the collection tray 130, to facilitate emptying debris from the apparatus 100, as needed.

In still further embodiments of the present invention, the cleaning apparatus 100 may comprise flexible hinge element 118, which allow the user to position the cleaning apparatus 100 at an angle that facilitates the gravimetric collection of debris within the collection tray 130, but also enables the user to position the device in an ergonomically favorable position. For example, a back surface of the device may reversibly connect to a first hinge 118 that allows the device to rotate around the long, longitudinal axis of the cleaning device. Further, the first hinge 118 may comprise a connection surface that attaches to a second hinge that is perpendicular to the first hinge, wherein the second hinge is attached either directly to a stationary object (e.g. table, desk, etc.), or the second hinge is attached to a second surface which is subsequently attached to a stationary object. A second hinged element 128 may also be provided to permit rotation about the lateral axis.

In some embodiments of the present invention, the cleaning apparatus 100 comprises a rectangular housing with a top end comprising an entry port or opening 111 therethrough. The interior volume of the housing preferably comprises two cylindrical brushes mounted at the same height along the long axis of the housing, wherein the axes of the cylindrical brushes are mounted between and perpendicular to the housing front and rear surfaces. In use, the user inserts the instrument to be cleaned through the opening 111 and between the two cylindrical brushes. This geometrical configuration permits the user to leave the instrument of other device in the cleaning device while continuing with other tasks. A flap 112 may further be provided to cover the opening 111.

Referring now to FIGS. 11-14, in one embodiment the cleaning apparatus 100 may further comprise a plurality of fluid injection ports and system of distributing at least one fluid from a fluid cartridge to the plurality of fluid injection ports. The system preferably comprises at least one pump 152 and tubing 154 interconnecting a fluid cartridge 150 to one or more nozzles 168, as shown in FIG. 13. The fluid may be a saline solution or may be sterile water or other suitable liquid for cleaning and lubricating a series of brushes 114. The nozzles are preferably positioned at the top of the housing and within the cleaning chamber, such that the fluid is injected into the cleaning apparatus 100 and by gravitational and rotational forces (applied by the brushes rotating in close proximity to the nozzles) passes towards the front or lower portion of the cleaning apparatus 100 and ultimately in contact with an instrument or device in the cleaning apparatus 100 and the brushes 114. In this manner, the liquid serves to both cleanse and purge debris and material from the instrument but also serves to lubricate and cleanse the brushes 114. The system may also comprise a sensor 164 which provides a signal to the pump 152 when the sensor detects that the brushes or the interior of the cleaning apparatus does not have adequate moisture. Various sensors known to those of ordinary skill in the art for achieving this sensing capability are considered within the scope of the present disclosure. The system also includes cylinders 122 associated with the brushes, which have been removed in FIG. 11

Referring now to FIGS. 14-20, one embodiment of the present disclosure relates to a cleaning apparatus comprising a housing that defines an internal volume, which holds a liquid, and wherein a mixing device 210 agitates the liquid. In some embodiments of the present invention, the housing 230 may comprise a top surface, a bottom surface, and at least one sidewall. In still further embodiments of the present invention, the housing 230 may comprise a cylindrical shape, wherein the top surface is substantially circular, the bottom surface is substantially circular, and wherein the top and bottom surfaces are connected by a vertical sidewall extending between the top and bottom surfaces.

In some embodiments of the present invention, the top surface may comprise an entry port 234 comprising an opening that passes through the top surface, to provide access to the internal volume of the housing 230. The entry port 234 may be an opening of a specific geometric shape, for example, but not limited to, a circular, oval, square, rectangular, or any other suitable shape sized to allow insertion of the device being cleaned into the cleaning portion of the device. In further embodiments of the present invention, the entry port 234 may comprise a cover over the opening. In some embodiments of the present invention, the entry port may comprise a cover constructed from a flexible, pliable, conformable, or bendable material with a hole or slot passing through the cover, to allow the instrument to be inserted therethrough. The cover may be sized to substantially cover the entire open surface area of the entry port 234 opening.

In some embodiments of the present invention, the entry port 234 may be an opening placed in the center of a circular top surface that is built into or attached to the top end of a cylindrical housing 230. In some further embodiments of the present invention, the entry port 234 may comprise a circular funnel-shaped structure in which the lower internal portion of the funnel-shaped structure terminates with a circular, oval, square, or rectangular opening. In still further embodiments of the present invention, the entry port 234 may comprise a funnel-shaped structure and a flexible cover with a hole therethrough, wherein the cover is positioned at the top, wide portion of the funnel.

In some embodiments of the present invention, the cleaning apparatus 200 retains a liquid inside at least a portion of the internal volume of the housing 230. In some of the embodiments of the present invention, a liquid is utilized to provide both mechanical cleaning and chemical cleaning to the instrument that is inserted into the liquid. In some embodiments of the present invention, a liquid may comprise at least one of water, an alcohol, an organic, a saline solution, an antiseptic, a preservative, formaldehyde, a stabilizer, an acid, a base, a solvent, and any other liquid for achieving a particular function of interest. In some further embodiments a liquid will fill all of or less than the internal empty volume of the cleaning apparatus 200. It should be clear to one of ordinary skill in the art, that embodiments of the present invention incorporating a liquid cleaning agent may preferably incorporate o-rings, gaskets, or seals into the connections between the various elements of the cleaning apparatus 200.

In some embodiments of the present invention, a mixing device 210 may comprise at least one of a jet, a nozzle, an agitator, an impeller, a turbine, a wheel, and any other suitable device for agitating or mixing the liquid contained in the cleaning apparatus 200. In some embodiments of the present invention, a mixing device 210 comprises a rotating device comprising at least one of an agitator, an impeller, a turbine, a wheel, and any other suitable rotating mixing device. In some embodiments of the present invention, a rotating device may utilized, comprising a shaft with a long axis, a first end, and a second end, with at least one surface attached to the shaft extending in a directions substantially perpendicular to the long axis of the shaft, wherein rotation of the shaft around its long axis rotates the at least one surface. Thus, when the at least one surface is submerged in the liquid, the at least one surface provides mechanical work to the liquid, and motion and mixing of the liquid within the housing 230.

In some embodiments of the present invention, a mixing device 210 for providing mixing is at least one of an axial flow impeller, a radial flow impeller, a Rushton turbine, a propeller, a paddle mixer, a turbine, a flat blade impeller, a pitched blade impeller, a curved blade impeller, an anchor impeller, and combinations thereof. In still further embodiments of the present invention, a mixing device 210 may comprise a water wheel agitator, wherein the water wheel comprises a circular outside member, with at least two spokes extending within the plane of the circular outside member, and the spokes extend from the outside circumference of the circular outside member, wherein the two spokes meet at a hub positioned at the center-point of the circular member, wherein the hub is also in the plane of the spokes. The water wheel agitator further comprises at least one rectangular-shaped mixing surface, connected to the outside circumference of the circular outside member, and extending upwards and perpendicular to the plane of the outside circular member.

In still further embodiments of the present invention, a water wheel agitator may comprise a bottom circular outside member and a top circular member, wherein the bottom circular outside member further comprises at least two spokes extending within the plane of the bottom circular outside member, and the spokes extend from the outside circumference of the bottom circular outside member, wherein the two spokes meet at a hub positioned at the center-point of the bottom circular outside member, wherein the hub is also in the plane of the bottom circular outside member. The water wheel agitator further comprises at least one rectangular-shaped mixing surface comprising a first end and a second end, wherein the first end of each mixing surface is connected to the outside circumference of the bottom circular outside member, and each mixing surface extends upwards and perpendicular to the plane of the outside circular member, and the second end of each mixing surface attaches to an outer circumference of the top circular outside member.

In some embodiments of the present invention, a water wheel agitator further comprises a shaft mounted perpendicularly to a hub 232, which may further comprise a coupling 248 and motor 246 for providing the mechanical drive necessary to set the mixing device 210 in motion, as illustrated in FIG. 18. In an alternative embodiment, illustrated in FIGS. 19-20, the apparatus 200 includes a mixing device 210 interconnected by coupling 254 to a motor 252 that is pneumatically driven. The motor 252 is supplied with a gas from gas supply 250. In some embodiments of the present invention, a mixing device 210 for providing mixing to the liquid retained inside the housing of the cleaning apparatus 200 may be attached to the housing by affixing the shaft of the mixing device 210 substantially to the center of the inside face of the bottom surface. In further embodiments of the present invention, the shaft may extend through a hole in the bottom surface, wherein o-rings, seals, or gaskets provide a liquid-tight seal to prevent liquid from leaking out of the housing internal volume. The shaft thus inserted through the bottom surface may then physically engage a motor such that the motor drives rotation of the shaft.

In still further embodiments of the present invention, the cleaning apparatus 200 may further comprise a base structure 240 that has substantially the same cross-sectional profile as the cross-sectional profile of the housing 230, wherein the housing 230 is aligned with, and place on top of, the base structure 240. Further, the motor and any other electronic and mechanical means may be placed within the base structure 240. In still further embodiments, a base structure 240 may comprise a top surface, a bottom surface, and sidewall extending between the top and bottom surfaces. The base structure 240 may further comprise a top port 244 for receiving the shaft or other coupling to mixing device 210. The base structure 240 may also comprise an aperture 242 for receiving an electrical or pneumatic power supply.

In still further embodiments of the present invention, the at least one mixing device 210 may comprise one, two, three, four, or five rotating devices, wherein each rotating device comprises a shaft that is affixed to the bottom surface of the housing, and wherein each shaft is rotated by a motor.

In some embodiments of the present invention, the mixing device 210 for cleaning the instrument may comprise at least one cylindrical brush, comprising a first end, a second end, and a length spanning the first and second ends, wherein the second end comprises a shaft that is affixed to the bottom surface of the housing and is driven by a motor. In such embodiments, the at least one brush may provide liquid mixing as well as brush surfaces for providing additional mechanical means of cleaning.

In still further embodiments of the present invention, the mixing device 210 may comprise at least one jet or nozzle. It will be understood by one of ordinary skill in the art, that embodiments utilizing at least one jet or nozzle will require a pressurized source of water. This may be provided by a "house" water supply; e.g. city water, or if higher pressures are required, by a pump provided by the cleaning apparatus. The disadvantage of using "house" water is that every volumetric unit of water added to the cleaning apparatus 200 will also need to be removed, whereas an internally located pump, provides the advantage of being able to reuse the internal volume of liquid of the apparatus itself. An internal pump also enables many more liquids to be used, besides water. In addition, the internal flow path of a pump, e.g. an inlet and an outlet, may provide a convenient means for providing a filter mechanism for removing the debris from the liquid, as it is removed from the instrument being cleaned.

In some embodiments of the present invention, the housing of a cleaning apparatus may further comprise a filter device 220, wherein the filter device 200 resides within the mixing device 210. In this embodiment, a pump (not shown) may discharges water through the pump's outlet. The outlet then leads to a nozzle or jet located within the cleaning apparatus housing, such that the water is re-injected into the housing through the nozzle and/or jet. In some embodiments of the present invention, the pump is a centrifugal pump or a positive displacement pump.

In some embodiments of the present invention, the housing of the cleaning apparatus maintains a housing volume that is less than 10% full of liquid and spray nozzles are used to clean the instrument. As above for the jet or nozzle embodiments, spray nozzles will also require a pressurized source of water.

In still further embodiments of the present invention, an ultrasound source may be provided to embodiments of the present invention wherein the housing is substantially full of liquid.

Referring now to FIG. 21, the cleaning apparatus further comprises a selectable attachment 300 for coupling the cleaning apparatus to an operating room table or other piece of furniture or stationary equipment in the operating room. According to this embodiment, the selectable attachment may be comprised of an arm with a first end coupled to the cleaning apparatus and positionable about a wide variety of axes and orientations, such as may be accomplished by a swivel or ball and socket connection between the arm and the cleaning apparatus. The arm according to this embodiment may further comprise a second end, which includes a coupling device capable of coupling the second end of the arm to a operating room table or other piece of furniture. In one embodiment, this coupling device is comprised of a clamp. In another embodiment, the coupling device is magnetic. In yet another embodiment, the coupling device is a vice. Several variations and combinations of coupling mechanisms known to those of skill in the art may be substituted for these preferred coupling devices without deviating from the novelty of the present disclosure, and are accordingly considered to be within the scope of the disclosure and the appended claims.

In some embodiments of the present invention, the cleaning apparatus may be attached to a securement device which enables the user to place the cleaning apparatus in a specific desire position or configuration relative to the work environment. In some embodiments of the present invention a securement device may comprise a flexible and/or moveable arm, wherein a first end of the arm is attached to a stationary object, e.g. a table, desk, counter, and a second end of the arm is attached to the cleaning apparatus.

In some embodiments of the present invention, the length of a moveable arm may be divided into a first length and a second length, which connect the stationary object to the cleaning apparatus. The distal end of the first length may terminate in a joint, which may attach to the proximal end of the second length. The proximal end of the first length may be pivotally coupled to a joint, which attaches to the stationary object for pivotal movement relative thereto. The first length may rotate a full 360 degrees around a vertical axis extending through the cleaning apparatus. In addition the joint located at the stationary object may also rotate upward out of the horizontal plane, up to 180 degrees. It should, however, be understood that the first length's degrees of rotational movement can have other values without departing from the scope of the present invention. The proximal end of the second length may attach to the distal end of the first length at a second joint. This second joint may comprise any articulating means known to one of ordinary skill in the art to allow the second length to rotate around the joint to any desirable position within three-dimensional space. For example, the second length may rotate a full 360 degrees in a plane around the second joint at the distal end of the first length. The second length may also rotate relative to the first length in a vertical plane.

It should, however, be understood that the second length horizontal and vertical rotation ranges and the first length horizontal and vertical rotation ranges, as well as their general movement within three-dimensional space, can be varied to suit the particular design and functional requirements of the user of the cleaning apparatus. Similarly, the specific lengths of the first and second lengths may have any desired specific values, as required by a user or environment.

Other embodiments of the present invention may entail securement devices comprising a single stationary arm, wherein one end of the arm is affixed to a point of rotation.

According to yet another embodiment, the selectable attachment may be comprised of a mechanism for attaching the cleaning apparatus to one or more surgical drapes. In one embodiment, this may be accomplished by a suitable combination of fabric, such as Velcro. According to other embodiments, the attachment may be accomplished via a plurality of oppositely charged magnets, which are separable and may be placed on opposite sides of the one or more drapes to secure the cleaning apparatus.

Regardless of the embodiment for attaching the cleaning apparatus to a table or other piece of furniture, the attachment is preferred to further comprise means for selectively establishing the height and/or orientation of the cleaning apparatus relative to the physician or other user of the cleaning apparatus. For example, the means may comprise one or more adjustable elements, such as a height position adjustment for securing the cleaning apparatus in a location ideal for the location the surgeon is standing, the surgeon height, right-handed versus left-handed dominance, preferred location relative to other equipment and the operating environment, etc. As another example, the adjustment may comprise the ability to permit the cleaning apparatus to rotate away from the operating site if no longer in use or temporarily unnecessary. The means described herein may be comprised of a telescoping mechanism, a C-arm mechanism, a simple-hinged mechanism, a pivot mechanism, a ball and socket mechanism, a living hinge mechanism, a set-screw mechanism, or a geared mechanism, among other types of adjustable mechanisms.

In another embodiment, the selectable attachment may further comprise the ability to rotate the orientation of the cleaning apparatus according to user preference, such that the receiving face of the cleaning apparatus is oriented facing up or facing to one lateral side or another lateral side. In this manner, the cleaning apparatus may be oriented to permit a surgeon to insert an instrument into the cleaning apparatus either in an upwardly facing receiving area or a laterally facing receiving area (i.e., parallel to the plane of the surgical field).

Another aspect of the present disclosure relates to maintaining the sterility of the surgical environment, and shielding the cleaning apparatus from the sterile field. For example, the cleaning apparatus may further comprise a shield or barrier to prevent material from leaving the instrument or other device to be cleaned by the cleaning apparatus in a direction other than internal to the cleaning apparatus and the collection tray. In this manner, for any instruments that are used and needing to be cleaned in the operating room, the surgeon or other medical professional may conveniently clean the instrument without accidentally removing fluid or debris from the instrument on the drape, the patient, the sterile zone, or otherwise exposing this non-sterile material onto other instruments or to the surgical site generally.

In one embodiment, the collection tray permits the collection of dry materials. In another embodiment, the collection is facilitated by a saline bath, which permits the material collected to be cleaned prior to collection. In a preferred embodiment, the collection tray resides near the bottom of the cleaning apparatus, so that material and debris collected during the cleaning operation passes through the brushes and into the collection tray by virtue of gravitational forces. The cleaning apparatus may comprise one or more filters, of varying granularity, to facilitate the separation of bone material, for example, from other material and fluid collected during the cleaning process. The filters may be removable for periodic cleaning and for removing the material from the filters.

The apparatus may comprise a particular entry portal for facilitating the placement of the instrument or other device to be cleaned by the apparatus. According to one particular embodiment, the instrument entry portal is oriented to grab and stabilize the instruments, which are often long and unbalanced, and permits the surgeon to leave the instrument in the cleaning apparatus for continued cleaning or to free his hands temporarily while he uses another instrument. A preferred embodiment having a duck bill entry portal is shown in FIG. 1, however, several alternately oriented entry portals may be provided without departing from the spirit of the present disclosure.

The apparatus disclosed herein may be made of a variety of different materials. These materials may include, by way of example but not limitation, stainless steel, titanium alloy, aluminum alloy, chromium alloy, and other metals or metal alloys. These materials may also include, for example, PEEK, carbon fiber, ABS plastic, polyurethane, resins, particularly fiber-encased resinous materials rubber, latex, synthetic rubber, synthetic materials, polymers, and natural materials.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials in appended Exhibit A hereto are expressly made a part of this disclosure and incorporated by reference herein in their entirety.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for cleaning, comprising:
   a housing;
   a removable cartridge selectively received within the housing;
   a plurality of brushes received within the housing;
   at least one filter received adjacent to the removable cartridge and in communication with a collection container;
   a biasing member coupled to the removable cartridge and contained within the housing;
   a first structure located on the housing, the first structure comprising a helical track along an interior surface of the housing;
   a second structure located on the removable cartridge, the second structure comprising at least one tab on an exterior surface of the removable cartridge, wherein the at least one tab may be received within the helical track;
   wherein the removable cartridge is configured to move within the housing between a first position and a second position;
   wherein the second structure is adapted to be received at least partially within the first structure when the cartridge is selectively received by the housing;
   wherein the movement of the second structure within the first structure creates a rotational movement of the removable cartridge relative to the housing; and
   wherein the biasing member biases the removable cartridge to the first position.

2. The device for cleaning of claim 1 further comprising an entry valve, the entry valve comprising a funnel having an opening therethrough, the opening in communication with an interior of the housing, and wherein the funnel is capable of being rotated about an axis transverse to the longitudinal axis of the housing.

3. The device for cleaning of claim 2, wherein the entry valve is adapted to receive at least one of an instrument, a tool, and an implant.

4. The device for cleaning of claim 2, wherein the entry valve further comprises a cover over a top surface of the funnel, wherein the cover comprises at least one aperture for inserting an instrument, tool or other device into the housing.

5. The device for cleaning of claim 1 further comprising at least one fluid injection port for injecting fluid into the housing.

6. The device for cleaning of claim 1 further comprising at least one exit port for draining fluid from the housing.

7. The device for cleaning of claim 1 further comprising an obstruction for preventing an instrument inserted into the device from being inserted beyond a predetermined depth.

8. The device for cleaning of claim 1, wherein the at least one filter separates reusable material from unusable material.

9. The device for cleaning of claim 1 further comprising a motor and a coupling for mechanically linking a shaft of the motor to the removable cartridge, wherein the cartridge rotates relative to the housing in response to a force received from the motor and movement of the second structure within the first structure.

10. The device for cleaning of claim 9, wherein the coupling for mechanically linking the shaft of the motor further couples to at least one of the plurality of brushes for rotating at least one of the plurality of brushes.

11. The device for cleaning of claim 9, wherein the motor is activated by a sensor and is activated once an instrument is inserted into the device in proximity to the sensor.

12. The device of cleaning of claim 9 further comprising at least one electrical actuator for activation of the motor.

13. The device for cleaning of claim 1 further comprising a pneumatic actuator and coupling for providing rotation to the removable cartridge by pneumatic means, wherein the cartridge rotates relative to the housing in response to a force received from the coupling and movement of the second structure within the first structure.

14. A device for cleaning, comprising:
   a housing, comprising a substantially hollow void within the housing;
   a cleaning cartridge selectively received within the hollow void;
   at least one brush adapted to be received within the cleaning cartridge;
   a biasing member, wherein the biasing member biases the cleaning cartridge towards a first position within the hollow void of the housing;
   wherein the cleaning cartridge is adapted to be moved from the first position to a second position within the hollow void of the housing through application of pressure placed upon a top surface of the cleaning cartridge;
   wherein the biasing member biases the cleaning cartridge to return to the first position once the application of pressure is removed; and
   wherein at least one of the movement of the cleaning cartridge from the first position to the second position or the movement of the cleaning cartridge from the second position to the first position causes the cleaning cartridge to rotate relative to the housing, and wherein the rotation of the cleaning cartridge further causes the at least one brush to rotate relative to the cleaning cartridge.

15. The device of claim 14 further comprising at least one filter attached to a lower end of the housing.

16. The device for cleaning of claim 14 further comprising an entry valve, the entry valve comprising a funnel having an opening therethrough, the opening in communication with the hollow void of the housing, and wherein the funnel is capable of being rotated about an axis transverse to the longitudinal axis of the housing.

17. The device for cleaning of claim 14 further comprising at least one fluid injection port for injecting fluid from a fluid container into the cleaning cartridge.

18. The device for cleaning of claim 14 wherein the at least one brush is arranged within the cleaning cartridge to permit placement of at least one instrument, tool or implant within the cleaning cartridge and contact the at least one brush.

19. The device for cleaning of claim 18 wherein the cleaning cartridge further comprises a bottom surface having a screen or filter for collecting materials removed from the at least one instrument, tool or implant.

20. A device for cleaning, comprising:
a housing;
an entry valve, the entry valve comprising a funnel having an opening therethrough, the opening in communication with an interior of the housing, wherein the funnel is capable of being rotated about an axis transverse to the longitudinal axis of the housing;
a removable cartridge selectively received within the housing;
a plurality of brushes received within the housing;
at least one filter received adjacent to the removable cartridge and in communication with a collection container;
a biasing member coupled to the removable cartridge and contained within the housing;
a first structure located on the housing;
a second structure located on the removable cartridge;
wherein the removable cartridge is configured to move within the housing between a first position and a second position;
wherein the second structure is adapted to be received at least partially within the first structure when the cartridge is selectively received by the housing;
wherein the movement of the second structure within the first structure creates a rotational movement of the removable cartridge relative to the housing; and
wherein the biasing member biases the removable cartridge to the first position.

21. A device for cleaning, comprising:
a housing;
a removable cartridge selectively received within the housing;
a plurality of brushes received within the housing;
at least one filter received adjacent to the removable cartridge and in communication with a collection container, wherein the at least one filter is operable to separate reusable material from unusable material;
a biasing member coupled to the removable cartridge and contained within the housing;
a first structure located on the housing;
a second structure located on the removable cartridge;
wherein the removable cartridge is configured to move within the housing between a first position and a second position;
wherein the second structure is adapted to be received at least partially within the first structure when the cartridge is selectively received by the housing;
wherein the movement of the second structure within the first structure creates a rotational movement of the removable cartridge relative to the housing; and
wherein the biasing member biases the removable cartridge to the first position.

* * * * *